US006953834B1

(12) United States Patent
DeJong

(10) Patent No.: US 6,953,834 B1
(45) Date of Patent: Oct. 11, 2005

(54) TRANSCRIPTION FACTORS RELATED TO TFIIA

(75) Inventor: Jeff L. DeJong, Richardson, TX (US)

(73) Assignee: Board of Regents, The University of Texas System, Austin, TX (US)

(*) Notice: Subject to any disclaimer, the term of this patent is extended or adjusted under 35 U.S.C. 154(b) by 157 days.

(21) Appl. No.: 09/703,809

(22) Filed: Oct. 30, 2000

Related U.S. Application Data

(62) Division of application No. 09/326,529, filed on Jun. 4, 1999.

(51) Int. Cl.⁷ ................................................ C07K 1/00

(52) U.S. Cl. ...................... 530/350; 435/183; 435/91.1; 435/6; 530/358

(58) Field of Search ................................ 435/194, 183; 530/350; 536/23.1, 23.2

(56) References Cited

U.S. PATENT DOCUMENTS

| | | | | |
|---|---|---|---|---|
| 5,652,117 | A | 7/1997 | Moore et al. | ............... 435/69.1 |
| 5,888,792 | A | 3/1999 | Bandman et al. | ............ 435/183 |
| 5,891,666 | A | 4/1999 | Matsuyama et al. | ........ 435/69.1 |
| 5,891,720 | A | 4/1999 | Moore et al. | ............... 435/325 |

OTHER PUBLICATIONS

Fry and Farnham, J. Biol. Chem. vol. 274, (42), pp 29583–29586, Oct. 1999.*
Ngo et al., Computational Complexity, Protein Structure Prediction, and the Levinthal Paradox, in The Protein Folding Problem and Tertiary Structure Prediction, 1994, Merz et al. (ed.), Birkhauser, Boston, MA, pp. 433 and 492–495.*
Marilyn Kozak, "Compilation and Analysis of Sequences Upstream from the Translational Start in Eukaryotic mRNAs," Nucleic Acids Research, vol. 12, No. 2, 1984, pp. 857–572.
Thomas A. Grigliatti, Linda Hall, Raja Rosenbluth and David T. Suzuki, "Temperature–Sensitive Mutations in Drosophila melanogaster XIV, A Selection of Immobile Adults," Molec. Gen. Genet. 120, 1973, pp. 107–114.
Christian A. Weideman, Robert C. Netter, Lawrence R. Benjamin, John J. McAllister, Lumelle A. Schmiedekamp, Robert A. Coleman and B. Franklin Pugh, "Dynamic Interplay of TFIIA, TBP and TATA DNA," J. Mol. Biol., 271, 1997, pp. 61–75.
Jeffrey A. Ranish, William S. Lane and Steven Hahn, "Isolation of Two Genes That Encode Subunits of the Yeast Transcription Factor IIA," Reports, Jan. 17, 1992, pp. 1127–1128.

Tetsuro Kokubo, Mark J. Swanson, Jun–Ichi Nishikawa, Alan G. Hinnebusch and Yoshihiro Nakatani, "The Yeast TAF145 Inhibitory Domain and TFIIA Competitively Bind to TATA–Binding Protein," Molecular and Cellular Biology, Feb. 1998, vol. 18, No. 2, pp. 1003–1012.

James H, Keen, "Clathrin and Associated Assembly and Disassembly Proteins," Annu. Rev. Biochem., 1990, pp. 415–438.

John J. Chicca II, David T. Auble and B. Franklin Pugh, "Cloning and Biochemical Characterization of TAF–172, a Human Homolog of Yeast Mot1," Molecular and Cellular Biology, Mar. 1998, vol. 18, No. 3, pp. 1701–1710.

Dong Kun Lee, Jeff DeJong, Shigeru Hashimoto, Masami Horikoshi and Robert G. Roeder, "TFIIA Induces Conformational Changes in TFIID via Interactions with the Basic Report," Molecular and Cellular Biology, Nov. 1992, vol. 12, No. 11, pp. 5189–5196.

Richard Bernstein, Jeff DeJong and Robert G. Roeder, "Characterization of the Highly Conserved TFIIA Small Subunit from Drosophila melanogaster," The Journal of Biological Chemistry, Sep. 30, 1994, vol. 269, No. 39, pp. 24361–24366.

Jennifer Hirst and Margaret S. Robinson, "Clathrin and Adaptors," Biochimica et Biophysica Acta 1404, 1998, pp. 173–193.

George Orphanides, Thierry Lagrange and Danny Reinberg, "The General Transcription Factors of RNA Ppolymerase II," Genes and Development, 1996, pp. 2657–2683.

(Continued)

Primary Examiner—Richard Hutson
(74) Attorney, Agent, or Firm—Chalker Flores, LLP; Edwin S. Flores; Chainey Singleton

(57) ABSTRACT

The invention provides human polynucleotide sequences that encode transcription factor polypeptides that are termed ALF and SALF, and an alternative C-terminal sequence. The invention includes ALF, SALF and alternative C-terminus polypeptides, peptides, fusion proteins, expression vectors, agonists, antagonists, host cells that overexpress these polypeptides, including transgenic animals, and recombinant knock-out animals that cannot express the relevant RNAs and polypeptides. The invention also provides methods for the detection, diagnosis, screening, and monitoring disorders related to inappropriate expression, production, or activity of ALF and SALF, and provides methods to increase or decrease gene expression with respect to treating disorders related to inappropriate or ineffectual patterns of gene expression.

1 Claim, 9 Drawing Sheets

OTHER PUBLICATIONS

Yasuhiro Nakayama, Mark Goebl, Betsy O'Brine Greco, Sandy Lemmon, Elizabeth Pinchang Chow and Tomas Kirchhausen, "The Medium Chains of the Mammalian Clathrin–Associated Proteins Have a Homolog in Yeast," J. Biochem, 1991, pp. 569–574.

Christophe Thurieau, Jurgen Brosius, Cindy Burne, Pierre Jolles, James H. Keen, Robert J. Mattaliano, E. Pingchang Chow, Kuzhal L. Ramachandran and Tomas Kirchhausen, "Molecular Cloning and Complete Amino Acid Sequence of AP50, an Assembly Protein Associated with ClathrinCoated Vesicles," DNA, vol. 7, No. 10, 1998, pp. 663–669.

James H. Geiger, Steve Hahn, Sally Lee and Paul B. Sigler, "Crystal Structure of the Yeast TFIIA/TBP/DNA Complex," Science, vol. 272, May 10, 1996, pp. 830–836.

Justen Andrews, Michiko Smith, John Merakovsky, Michelle Coulson, Frances Hannan and Leonard E. Kelly, The Stoned Locus of Drosophila melangaster Produces a Dicistronic Transcript and Encodes Two Distint Polypeptides, Genetics, Aug. 1996, pp. 1699–1711.

Weidong Wang, Jay D. Gralla and Michael Carey, "The Acidic Activator GAL4–4H Can Stimulate Polymerase II Transcription by Promoting Assembly of a Closed Complex Requiring TFIID and TFIIA," Genes and Development, 1992, pp. 1716–1727.

Paul M. Lieberman and Arnold J. Berk, "A Mechanism for TAFs in Trancriptional Activation: Activation Domain Enhancement of TFIID–TFIIA–Promoter DNA Complex Formation," Genes & Development, 1994, pp. 995–1006.

Katayoon H. Emami, Anjali Jain and Stephen T. Smale, "Mechanism of Synergy Between TATA and Initiator: Synergistic Binding of TFIID Following a Putative TFIIA–Induced Isomerization," Genes & Development, 1997, pp. 3007–3019.

Tianhuai Chi and Michael Carey, "Assembly of the Isomerized TFIIA, TFIID–TATA Ternary Complex is Necessary and Sufficient for Gene Activation," Genes & Development, 1996, pp. 2540–2550.

Bejamin M. Shykind, Jaesang Kim and Phillip A. Sharp, "Activation of the TFIID–TFIIA Complex with HMG–2," Genes & Development, 1995, pp. 1354–1365.

David T. Auble, Karin E. Hansen, Chris G.F. Mueller, William S. Lane, Jeremy Thorner and Steven Hahn, "Mot1, a Global Représsor of RNA Polymerase II Transcriptiona, Inhibits TBP Binding to 'DNA by an ATP–Dependent Mechanism," Genes & Development, 1994, pp. 1920–1934.

Josef Ozer, Paul A. Moore, Arthur H. Bolden, Arianna Lee, Craig A. Rosen and Paul M. Lieberman, "Molecular Cloning of the Small (y) subunit of Human TFIIA Reveals Functions Critical for Activated Transcription," Genes & Development, 1994, pp. 2324–2335.

Xiaoqing Sun, Dongmin Ma, Michael Sheldon, Jam Yeung and Danny Reinberg, "Reconstitution of Human TFIIA Activity from Recombinant Polypeptides: A Role in TFIID-Mediated Transcription," Genes and Development, 1994, pp. 2336–2348.

David T. Auble and Steven Hahn, "An ATP–Dependent Inhibitor of TBP Binding to DNA," Genes & Development, 1993, pp. 844–856.

Jeff DeJong and Robert G. Roeder, "A Single eDNA, hTFIIA/a, Encodes Both the P35 and p19 Subunits of Human TFIIA," Genes & Development, 1993, pp. 2220–2234.

Kyoko Yokomori, Arie Admon, James A. Goodrich, JinLong Chen and Robert Tjian, "Drosophila TFIIA–L is Processed Into Two Subunits that are Associated with the TBP/TAF Complex," Genes & Development, 1993, pp. 2235–2245.

Dongmin Ma, Hajime Watanabe, Fred Memelstein, Arie Admon, Kiyoshi Oguri, Ziaoqing Sun, Tadashi Wada, Takeshi Imai, Toshifumi Shiroya, Danny Reinberg and Hiroshi Handa, "Isolation of cDNA Encoding the Largest Subunit of TFIIA Reveals Functions Important for Activated Transcription," Genes & Development, 1993, pp. 2246–2257.

Robert G. Roeder, "The Role of General Initiation Factors in Transcription by RNA Polymerase II," Elsevier Science Ltd. 1996, pp. 327–335.

Nikolai C Kirov, Paul M. Lieberman and Christine Rushlow, "The Transcriptional Corepressor DSP1 Inhibits Activated Transcription by Disrupting TFIIQ TDP Complex Formation," The EMBO Journal, vol. 15, No. 24, 1996, pp. 7079–7087.

Jeff DeJong, Richard Bernstein and Robert G. Roeder, "Human General Transcriptional Factor TFIIA: Characterization of a cDNA Encoding the Small Subunit and Requirement for Basal and Activated Transcription," Proc. Natl, Acad. Sci., vol. 92, Apr. 1995, pp. 3313–3317.

Dongmin Ma, Ivan Olave, Alejandro Merino and Danny Reinberg, "Separation of the Transcriptional Coactivator and Antirepression Functions of Transcription Factor IIA," Proc. Natl. Acad. Sci., Jun. 1996, vol. 93, pp. 6583–6588.

Josef Ozer, Arthur H. Bolden and Paul M. Lieberman, "Transcription Factor IIA Mutations Show Activator–Specific Defects and Reveal a IIA Function Distinct from Stimulation of TBP–DNA Binding," The Journal of Biological Chemistry, vol. 271, No. 19, May 10, 1996, pp. 11182–11190.

Josef Oser, Katherine Mitsouras, Dennis Zerby, Michael Carey and Paul M. Lieberman, "Transcription Factor IIA Derepresses TATA–Binding Protein (TBP)–Associated Factor Inhibition of TBP–DNA Binding," The Journal of Biological Chemistry, vol. 273, No. 23, 1998, pp. 14293–14300.

Hui Ge and Robert G. Roeder, "The High Mobility Group Protein HMG1 Can Reversibly Inhibit Class II Gene Transcription by Interaction with the TATA–Binding Protein," The Journal of Biological Chemistry, vol. 269, No. 25, Jun. 24, 1994, pp. 17136–17140.

Anthony N. Imbalzano, Kenneth S. Zaret and Robert E. Kingston, "Transcription Factor (TF) IIB and TFIIA Can Independently Increase the Affinity of the TATA–Binding Protein for DNA," The Journal of Biological Chemistry, vol. 269, No. 11, Mar. 18, 1994, pp. 8280–8286.

R. Wilson, et al., "2.2Mb of Contiguous Nucleotide Sequence from Shromosome III of C. Elegans," Nature, vol. 368, Mar. 3, 1994, pp. 32–38.

Thomas Oelgeschlager, Cheng–Ming Chiang and Robert G. Roeder, "Topology and Reorganization of a Human TFIID—Promoter Complex," Nature, vol. 382, Aug. 22, 1996, pp. 735–738.

Alejandro Merino, Knut R. Madden, Williams S. Lane, James J. Champoux and Danny Reinberg, "DNA Topoismerase I is Involved in Both Repression and Activation of Transcription," Nature, vol. 365, Sep. 16, 1993, pp. 227–232.

Song Tan, Yvonne Hunziker, David F. Sargent and Timothy J. Richmond, "Crystal Structure of a Yeast TFIIA/TBP/DNA Complex," Nature, vol. 381, May 9, 1996, pp. 127–134.

Hui Ge and Robert G. Roeder, "Purification, Cloning, and Characterization of a Human Coactivator, PC4, that Mediates Transcriptional Activation of Class II Genes," Cell, vol. 78, Aug. 12, 1994, pp. 513–523.

Juan A. Inostroza, Fred H. Mermelstein, Ilho Ha, William S. Lane and Danny Reinberg, "Dr1, a TATA–Binding Protein-Associated Phosphoprotein and Inhibitor of Class II Gene Transcription," Cell, vol. 70, Aug. 7, 1992, pp. 477–489.

Michael Meisterernst and Robert G. Roeder, "Family of Proteins that Interact with TFIID and Regulate Promoter Activity," Cell, vol. 67, No. 1, 1992, pp. 557–567.

Stephen Buratowski, Steven Hahn, Leonard Guarente and Phillip A. Sharp, "Five Intermediate Complexes in Transcription Initiation by RNA Polymerase II," Cell, vol. 56, Feb. 24, 1989, pp. 549–561.

Ashok B. Upadhyaya, Sang Hyun Lee, and Jeff DeJong; *The Journal of Biological Chemistry*, 1999, by the American Society of Biochemistry and Molecular Biology, Inc.; *Identification of a General Transcription Factor TFIIA $\alpha/\beta$ Homolog Selectivitely Expressed in Testis*\*; vol. 274, No. 25, Issue of Jun. 18, pp. 18040–18048, 1999.

\* cited by examiner

```
GCTGGAGGTGCTGTCATGGCCTGCCTCAACCCGGTGCCTAAACTCTACAGATCTGTAATTGAAGATGTAATTGAAGGAGT
TCGGAATCTATTTGCTGAAGAAGGTATAGAGGAACAAGTTTTAAAAGACTTGAAGCAGCTCTGGGAAACCAAGGTTTTGC
AGTCTAAAGCAACAGAAGACTTCTTCAGAAATAGCATCCAATCACCTCTGTTTACTCTTCAGTTGCCGCACAGCTTGCAC
CAAACATTGCAATCGTCAACAGCATCATTAGTTATTCCTGCTGGTAGAACTCTTCCAAGTTTTACCACAGCAGAACTGGG
CACTTCAAACTCCAGTGCAAACTTTACTTTTCCTGGTTATCCCATTCATGTACCAGCAGGTGTGACACTACAGACTGTAT
CTGGTCACCTTTATAAAGTCAATGTACCAATTATGGTGACAGAGACTTCTGGAAGAGCAGGTATTCTTCAGCATCCAATT
CAGCAAGTATTTCAACAGCTTGGCCAGCCTTCAGTAATACAAACTAGTGTTCCACAATTGAATCCATGGTCTCTTCAAGC
AACTACTGAAAAATCACAGAGAATTGAAACCGTGCTACAGCAACCCGCAATTCTACCTTCTGGGCCAGTAGATAGGAAAC
ACTTAGAAAATGCCACCAGTGATATACTTGTATCTCCTGGAAATGAGCATAAAATCGTGCCTGAAGCTTTGTTGTGTCAT
CAGGAAAGTTCTCACTATATCAGTCTTCCAGGTGTTGTATTTTCTCCACAGGTCTCTCAAACAAATTCTGATGTGGAGTC
AGTGCTCACTGGTTCAGCTAGCATGGCTCAAAATCTGCATGATGAGTCCCTCTCCACAAGCCCTCATGGGGCTCTCCACC
AGCACGTGACTGATATTCAGCTTCATATTCTTAAAAATAGGATGTATGGATGTGATTCTGTAAAGCAACCAAGAAATATA
GAGGAACCCAGCAACATACCTGTATCAGAGAAGGATTCTAATTCTCAGGTGGATTTAAGCATTCGGGTTACTGATGATGA
TATTGGTGAAATAATTCAAGTAGATGGAAGCGGTGATACATCTTCCAATGAAGAAATAGGAAGTACAAGAGATGCAGATG
AGAATGAATTTCTAGGGAATATTGACGGGGGAGATCTGAAGGTACCTGAAGAAGAAGCTGACAGTATTTCAAATGAGGAT
TCAGCCACAAACAGTAGTGATAATGAAGACCCTCAAGTAAACATTGTAGAAGAGGACCCTTTAAATTCTGGAGATGATGT
TAGTGAACAGGATGTGCCAGACCTGTTTGACACGGATAATGTAATTGTCTGTCAGTATGATAAGATTCATCGAAGCAAGA
ACAAATGGAAATTCTATTTGAAAGATGGTGTTATGTGTTTGGAGGGAGAGACTATGTATTTGCAAAAGCCATTGGTGAT
GCAGAGTGGTAAACCTTGTGAGCTCAGTACATCTATTTTGTGAACATCAGTTGGACTATATTGCATATTGTGAATTCATT
TTTATTTTGAATATAGTCCAGCACAGAGCTGTTCAAATTTTTAGTTCACTGTATGGAATTTAATAAAATTATAATTCAGA
TGCAGATACAATTACAC
```

Figure 1.

```
MACLNPVPKLYRSVIEDVIEGVRNLFAEEGIEEQVLKDLKQLWETKVLQSKATEDFFRNSIQSPLFTLQLPHSLHQTLQS
STASLVIPAGRTLPSFTTAELGTSNSSANFTFPGYPIHVPAGVTLQTVSGHLYKVNVPIMVTETSGRAGILQHPIQQVFQ
QLGQPSVIQTSVPQLNPWSLQATTEKSQRIETVLQQPAILPSGPVDRKHLENATSDILVSPGNEHKIVPEALLCHQESSH
YISLPGVVFSPQVSQTNSDVESVLSGSASMAQNLHDESLSTSPHGALHQHVTDIQLHILKNRMYGCDSVKQPRNIEEPSN
IPVSEKDSNSQVDLSIRVTDDDIGEIIQVDGSGDTSSNEEIGSTRDADENEFLGNIDGGDLKVPEEEADSISNEDSATNS
SDNEDPQVNIVEEDPLNSGDDVSEQDVPDLFDTDNVIVCQYDKIHRSKNKWKFYLKDGVMCFGGRDYVFAKAIGDAEW
```

Figure 2.

```
GGACTTTGGGACTGGACAGACCTGGTCACAGTCTAGGTTCTACATCTTACTGGTCGAGCAACTTTAGAGTCAACCTATTT
GATTTCTTGACAAGACCACAATCTGATCCCAAAGATGTGCTCCACAAATCCAGGCAAATGGGTCACCTTTGATGATGATC
CTGCTGTTCAATCTTCTCAAAAGTCAAAGAATTTTCCTCTGGAGAATCAAGGTGTCTGTAGACCCAAATGGACTGAAGCTG
AACCCTCCTGGCCTCAGGGAATTTCCCAGTGGATCTTCCTCCACCAGCAGCACTCCTCTCTCCTCCCCCATTGTAGATTT
TTATTTCAGTCCAGGACCTCCAAGTAACTCTCCTCTTTCTACACCTACCAAAGACTTCCCAGGTTTTCCTGGCATCCCCA
AAGCAGGGACTCATGTGCTTTATCCTATTCCAGAATCATCTTCAGACAGCCCACTCGCAATATCAGGAGGAGAATCTTCC
TTACTGCCTACCAGACCAACATGTTTATCCCATGCCTTGTTACCCAGTGACCACTCATGTACACATCCAACTCCCAAAGT
AGGTCTTCCAGATGAAGTTAATCCTCAACAGGCTGAAAGCCTAGGATTCCAAAGTGATGATCTCCCCCAGTTTCAGTATT
TTCGAGAGGACTGTGCTTTTTCAAGTCCATTTCGGAAAGATGAAGGCAGTGATTCCCATTTCACCCTTGACCCACCAGGA
AGCAAAAGATGTTCTCATCAAGAAACAAGGAGATGCCTATTGACCAAAAAAGCCTAAATAAGTGTTCACTCAACTATAT
CTGTGAGAAGCTTGAACATCTCCAGTCAGCTGAGAACCAAGACTCACTTAGAAGTTTGTCTATGCACTGTCTATGTGCTG
AAGAAAATGCCTCTTCCTTTGTCCCCCACACACTCTTCAGGAGTCAGCCAAAATCCGGATGGTCTTTCATGCTGAGAATT
CCTGAGAAGAAGAATATGATGTCTTCCCGGCAATGGGGACCAATTTTTCTGAAAGTTTTGCCTGGAGGAATTTTGCAGAT
GTATTATGAACAGGGATTAGAAAAACCATTTAAAGAGATACAGCTTGATCCATATTGTAGGCTTTCTGAACCCAAGGTTG
AGAACTTCAGTGTAGCAGGAAAAATCCACACTGTGAAGATTGAACATGTGTCTTACACAGAAAAAAGGAAATACCATTCT
AAGACAGAAGTAGTTCATGAACCTGACATAGAGCAGATGCTGAAGTTGGGGTCCACATCGTACCATGACTTCCTTGACTT
TCTGACTACTGTGGAGGAGGAGCTGATGAAGTTGCCAGCTGTTTCAAAACCAAAAAAGAACTACGAGGAGCAAGAAATTT
CCTTGGAAATTGTGGACAACTTTTGGGGTAAAGTCACAAAAGAAGGAAAATTTGTTGAAAGTGCTGTGATAACTCAAATT
TATTGCCTCTGCTTTGTGAATGGGAACCTGGAATGCTTTTTAACCTTGAATGACCTTGAGTTGCCGAAGCGAGATGAATC
CTATTATGAGAAGGACTCAGAAAAAAAGGGGATTGATATTCTTGACTACCATTTTCATAAGTGTGTGAATGTACAAGAAT
TTGAGCAATCAAGAATCATTAAGTTTGTACCTCTGGATGCCTGCCGGTTTGAGCTGATGCGTTTCAAGACTTTGTATAAT
GGGGATAATCTTCCCTTTTCCTTGAAGTCTGTAGTGGTTGTCCAGGGAGCATACGTGGAACTTCAGGCTTTTGTCAACAT
GGCCTCATTGGCGCAGAGGTCATCCTATGCTGGTTCCTTAAGGTCCTGTGACAATATAAGGATACACTTTCCTGTCCCAT
CGCAGTGGATCAAGGCCCTTTGGACCATGAACCTCCAGAGGCAGAAGTCTCTGAAAGCTAAAATGAACCGCCGAGCATGT
CTGGGGAGTTTACAGGAACTTGAATCTGAACCTGTCATTCAAGTCACTGTGGGGTCAGCAAAATATGAGAGTGCCTACCA
GGCAGTGGTATGGAAGATAGATCGGCTTCCAGACAAAAATTCAAGTCTAGATCATCCCCATTGTCTGTCATACAAATTAG
AGCTTGGATCAGACCAAGAAATTCCCTCTGATTGGTATCCATTTGCTACTGTTCAGTTTTCCGTGCCTGACACCTGTGCC
TCAAGGACAGAGGTCAGGTCTCTGGGAGTGGAGAGTGATGTCCAGCCACAGAAAACATGTTCAGCAGCGAGCTTGCTACAA
CATCCAGCCTAAACTCTACAGATCTGTAATTGAAGATGTAATTGAAGGAGTTCGGAATCTATTTGCTGAAGAAGGTATAG
AGGAACAAGTTTTAAAAGACTTGAAGCAGCTCTGGGAAACCAAGGTTTTGCAGTCTAAAGCAACAGAAGACTTCTTCAGA
AATAGCATCCAATCACCTCTGTTTACTCTTCAGTTGCCGCACAGCTTGCACCAAACATTGCAATCGTCAACAGCATCATT
AGTTATTCCTGCTGGTAGAACTCTTCCAAGTTTTACCACAGCAGAACTGGGCACTTCAAACTCCAGTGCAAACTTTACTT
TTCCTGGTTATCCCATTCATGTACCAGCAGGTGTGACACTACAGACTGTATCTGGTCACCTTTATAAAGTCAATGTACCA
ATTATGGTGACAGAGACTTCTGGAAGAGCAGGTATTCTTCAGCATCCAATTCAGCAAGTATTTCAACAGCTTGGCCAGCC
TTCAGTAATACAAACTAGTGTTCCACAATTGAATCCATGGTCTCTTCAAGCAACTACTGAAAAATCACAGAGAATTGAAA
CCGTGCTACAGCAACCCGCAATTCTACCTTCTGGGCCAGTAGATAGGAAACACTTAGAAAATGCCACCAGTGATATACTT
GTATCTCCTGGAAATGAGCATAAAATCGTGCCTGAAGCTTTGTTGTGTCATCAGGAAAGTTCTCACTATATCAGTCTTCC
AGGTGTTGTATTTTCTCCACAGGTCTCTCAAACAAATTCTGATGTGGAGTCAGTGCTCAGTGGTTCAGCTAGCATGGCTC
AAAATCTGCATGATGAGTCCCTCTCCACAAGCCCTCATGGGGCTCTCCACCAGCACGTGACTGATATTCAGCTTCATATT
CTTAAAAATAGGATGTATGGATGTGATTCTGTAAAGCAACCAAGAAATATAGAGGAACCCAGCAACATACCTGTATCAGA
GAAGGATTCTAATTCTCAGGTGGATTTAAGCATTCGGGTTACTGATGATGATATTGGTGAAATAATTCAAGTAGATGGAA
GCGGTGATACATCTTCCAATGAAGAAATAGGAAGTACAAGAGATGCAGATGAGAATGAATTTCTAGGGAATATTGACGGG
GGAGATCTGAAGGTACCTGAAGAAGAAGCTGACAGTATTTCAAATGAGGATTCAGCCACAAACAGTAGTGATAATGAAGA
CCCTCAAGTAAACATTGTAGAAGAGGACCCTTTAAATTCTGGAGATGATGTTAGTGAACAGGATGTGCCAGACCTGTTTG
ACACGGATAATGTAATTGTCTGTCAGTATGATAAGATTCATCGAAGCAAGAACAAATGGAAATTCTATTTGAAAGATGGT
GTTATGTGTTTTGGAGGGAGACTATGTATTTGCAAAAGCCATTGGTGATGCAGAGTGGTAAACCTTGTGAGCTCAGTA
CATCTATTTTGTGAACATCAGTTGGACTATATTGCATATTGTGAATTCATTTTTATTTTGAATATAGTCCAGCACAGAGC
TGTTCAAATTTTTAGTTCACTGTATGGAATTTAATAAAATTATAATTCAGATGCAGATACAATT
```

Figure 3.

```
MCSTNPGKWVTFDDDPAVQSSQKSKNFPLENQGVCRPNGLKLNPPGLREFPSGSSSTPLSSPIVDFYFSPGFPSNSP
LSTPTKDFPGFPGIPKAGTHVLYPIPESSSDSPLAISGGESSLLPTRPTCLSHALLPSDHSCTHPTPKVGLPDEVNPQQA
ESLGFQSDDLPQFQYFREDCAFSSPFTRKDEGSDSHFTLDPPGSKKMFSSRNKEMPIDQKSLNKCSLNYICEKLEHLQSAE
NQDSLRSLSMHCLCAEENASSFVPHTLFRSQPKSGWSFMLRIPEKKNMMSSRQWGPIFLKVLPGGILQMYYEQGLEKPFK
EIQLDPYCRLSEPKVENFSVAGKIHTVKIEHVSYTEKRKYHSKTEVVHEPDIEQMLKLGSTSYHDFLDFLTTVEEELMKL
PAVSKPKNYEEQEISLEIVDNFWGKVTKEGKFVESAVITQIYCLCFVNGNLECFLTLNDLELPKRDESYYEKDSEKKGI
DILDYHFHKCVNVQEFEQSRIIKFVPLDACRFELMRFKTLYNGDNLPFSLKSVVVVQGAYVELQAFVNMASLAQRSSYAG
SLRSCDNIRIHFPVPSQWIKALWTMNLQRQKSLKAKMNRRACLGSLQELESEPVIQVTVGSAKYESAYQAVVWKIDRLPD
KNSSLDHPHCLSYKLELGSDQEIPSDWYPFATVQFSVPDTCASRTEVRSLGVESDVQPQKHVQQRACYNIQPKLYRSVIE
DVIEGVRNLFAEEGIEEQVLKDLKQLWETKVLQSKATEDFFRNSIQSPLFTLQLPHSLHQTLQSSTASLVIPAGRTLPSF
TTAELGTSNSSANFTFPGYPIHVPAGVTLQTVSGHLYKVNVPIMVTETSGRAGILQHPIQQVFQQLGQPSVIQTSVPQLN
PWSLQATTEKSQRIETVLQQPAILPSGPVDRKHLENATSDILVSPGNEHKIVPEALLCHQESSHYISLPGVVFSPQVSQT
NSDVESVLSGSASMAQNLHDESLSTSPHGALHQHVTDIQLHILKNRMYGCDSVKQPRNIEEPSNIPVSEKDSNSQVDLSI
RVTDDDIGEIIQVDGSGDTSSNEEIGSTRDADENEFLGNIDGGDLKVPEEEADSISNEDSATNSSDNEDPQVNIVEEDPL
NSGDDVSEQDVPDLFDTDNVIVCQYDKIHRSKNKWRFYLKDGVMCFGGRDYVFAKAIGDAEW
```

Figure 4.

```
GCATTCCCAAGAAGGACATCGTTTAACACCTAAACTCATTTAACAAAGGATCCGAGAAGAACAGGGACAGTGTGGGAAGA
AATCTTCTTGTGATGGCATATTTGCTTCCTATATTTCTTCTGGAATCATGTTCGCTTGGCTTCCTGATTAAAAACACAGT
TTTATTGCTCTCTGCACTGCCAAACCAATAAATTTACAGAAGAGAAAGCTGTATTCCACTGTACCCCTTGCAGCATCAAT
AAAACTGACAGCC
```

Figure 5.

```
AFPRRTSFNT
```

Figure 6.

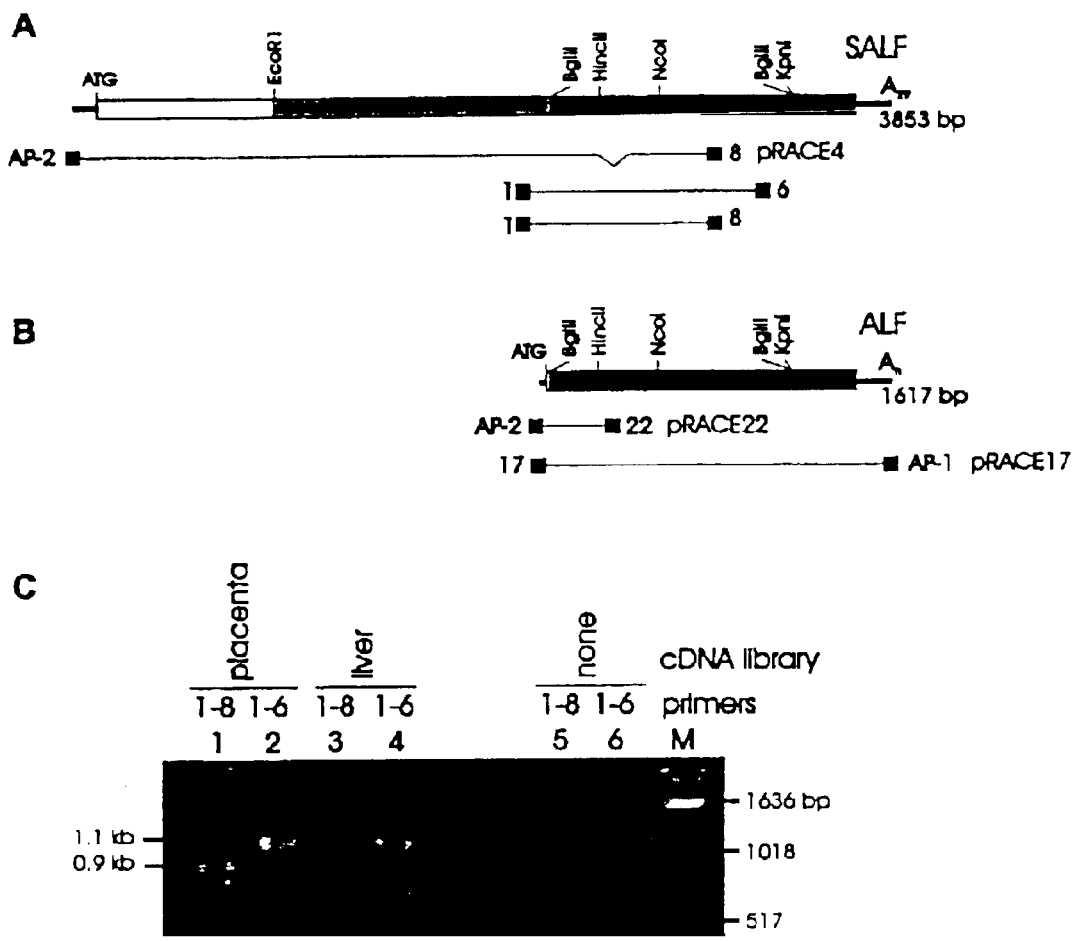
FIG 7 A-C

A

B

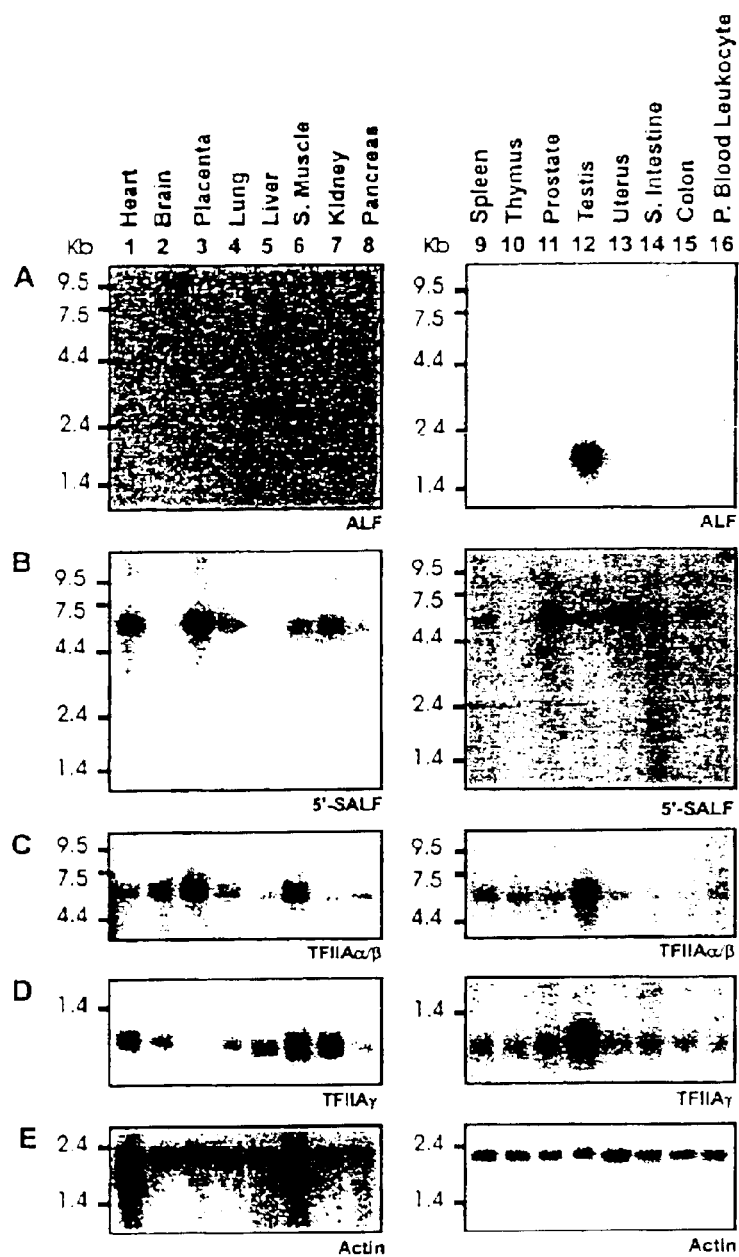
FIG 10 A-E

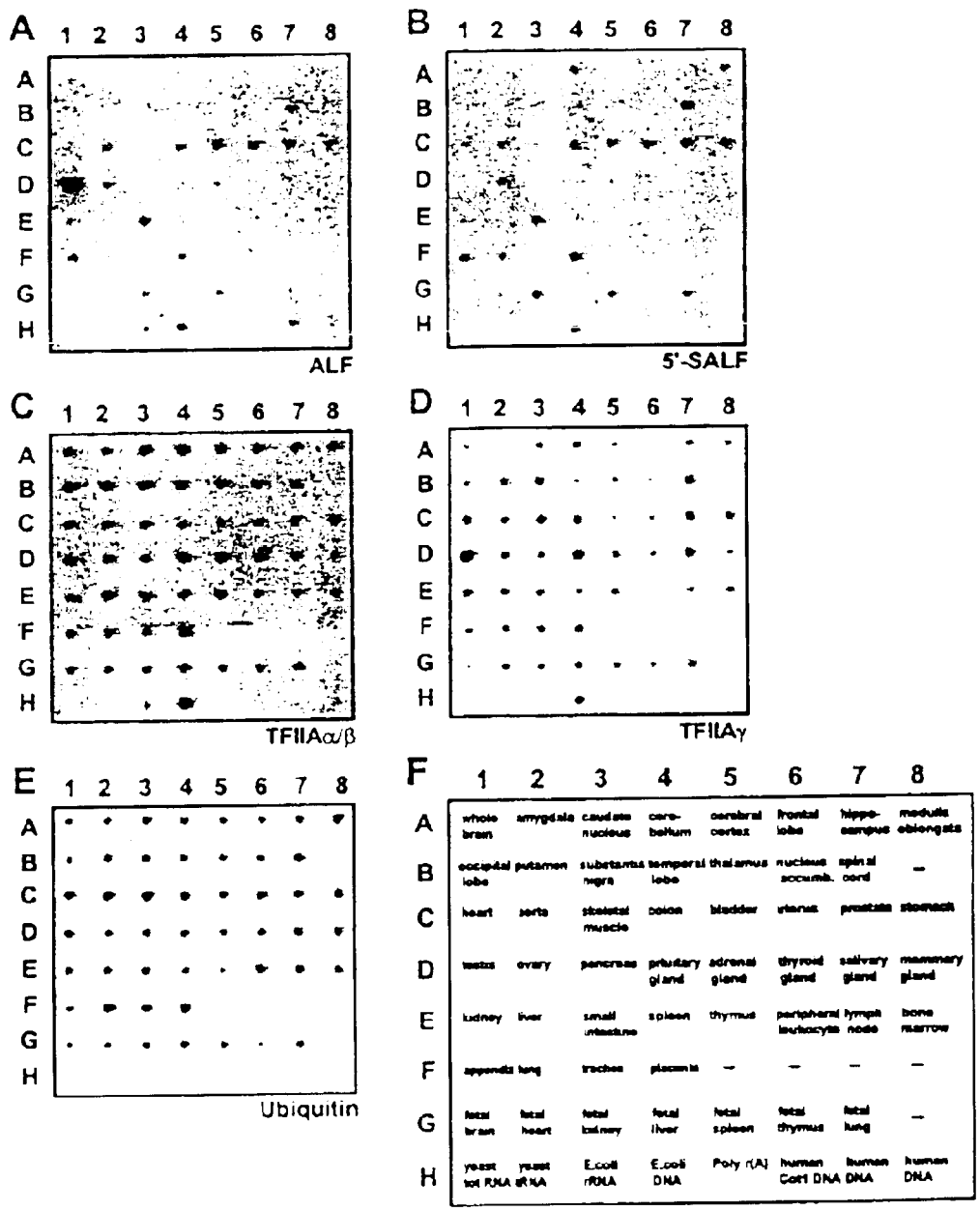
FIG 11 A-F

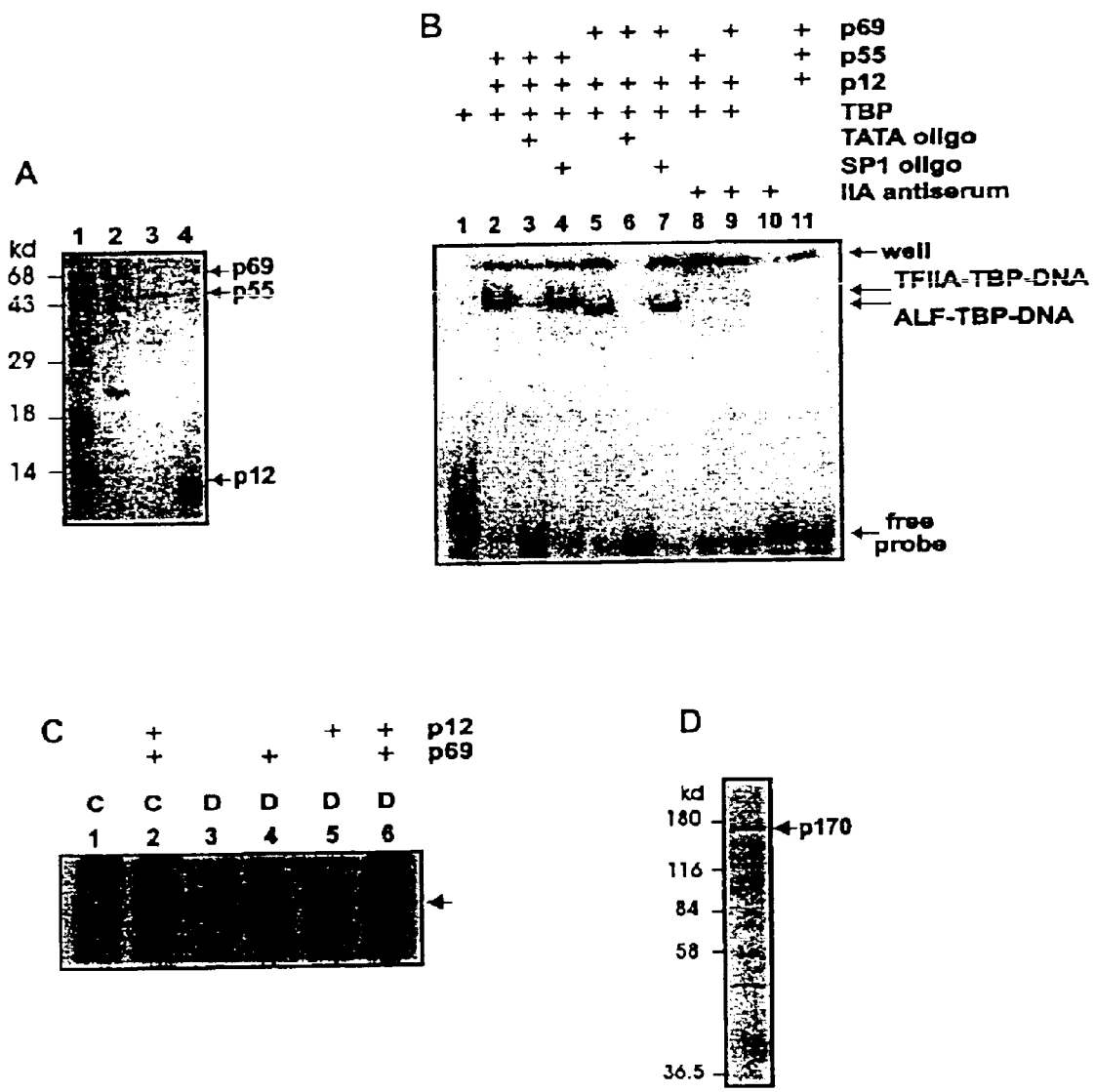
FIG 12 A-D

TRANSCRIPTION FACTORS RELATED TO TFIIA

This application is a division of pending application Ser. No. 09/326,529, filed on Jun. 4, 1999.

TECHNICAL FIELD OF THE INVENTION

The present invention relates in general to the field of recombinant nucleic acids, polypeptides and other derived materials and, more particularly, to the identification, isolation and characterization of human transcription factors that are involved in the expression of human genes.

BACKGROUND OF THE INVENTION

Without limiting the scope of the invention, its background is described in connection with the isolation, characterization and use of human transcription factors that are expressed throughout the organism, as an example.

Unlike the nucleic acid polymerases of prokaryotes, purified RNA polymerase II from eukaryotes initiates transcription very poorly and essentially at random. One key difference between prokaryotic and eukaryotic polymerases is the need for accessory factors that provide for the accurate initiation of transcription. These factors are referred to as the "general" or "basal" transcription factors, in that they are required, in addition to RNA polymerase II, for the transcription of all eukaryotic protein coding genes. As such, the general transcription factors are expected to be active, or at least present, in all or most tissues. One such general factor is called transcription factor IID (TFIID) and is responsible in large part for promoter recognition. Other general transcription factors include TFIIA, TFIIB, TFIIE, TFIIF and TFIIH.

Appropriate levels of gene and tissue-specific transcription is achieved by another set of factors called activator proteins. These factors are often composed of two domains, a sequence-specific DNA recognition domain and an activation domain. When bound to DNA, the activation domain facilitates the formation and function of a preinitiation complex that consists of the general transcription factors and RNA polymerase II. In this way it is possible to direct the selective transcription of genes in an appropriately regulated fashion.

The structure of a typical promoter for a eukaryotic gene consists of two general regions. The core promoter is located at or near the actual site of transcription initiation and often includes a TATA sequence element located at about 30 base pairs upstream of the initiation site. The other regions are defined as sequence elements which are recognized by activator proteins. These are often located at various distances further upstream, but may be also be located downstream relative to the core promoter of the gene being regulated. Interactions between bound regulatory factors and the preinitiation complex are responsible for the precisely regulated transcription of each individual gene.

TFIIA is an essential general transcription factor and the purified factor from higher eukaryotes consists of three subunits, designated alpha (35 kD), beta (19 kD) and gamma (12 kD). In humans, the alpha and beta subunits are encoded by DNA sequences present in the TFIIAα/β cDNA, sometimes referred to as the 'large' subunit cDNA. These two subunits are post-translationally processed from a large 55 kD product of TFIIAα/β. The gamma subunit is encoded by DNA sequences present in the TFIIAγ cDNA, sometimes referred to as the 'small' subunit cDNA. This sequence is the subject of U.S. Pat. No. 5,562,117 issued to Moore and Rosen. TFIIA has multiple roles in transcription initiation by RNA polymerase II, including an ability to stabilize TBP-TATA element interactions, displace TBP-associated repressors and serve as a cofactor during the processes of transcription activation.

Most of the known human general transcription factors appear to be generally required in all tissues for gene expression by RNA polymerase II. Thus, these factors will be important as markers to evaluate disease states which may arise from inappropriately regulated gene expression and as pharmacological reagents and/or targets with which to modulate patterns of gene expression. Similarly, overexpression via gene therapy or other means should have broad effects on the expression of many or all cellular genes. In contrast, mutations in the genes for activator proteins, which are normally observed to control expression of a select set of genes, often in a tissue or developmentally restricted pattern, typically result in specific defects. Likewise, overexpression of activator proteins only affects expression of cellular genes which contain cognate recognition sequences.

Testis has important endocrine (hormonal) functions and is the site for the production of haploid spermatozoa from undifferentiated stem cells, a process called spermatogenesis. Mutations in some specialized transcription activator proteins, such as A-myb and CREM, cause male infertility and show defects in spermatogenesis. The identification of tissue-specific human general transcription factor would bridge an important gap between the generality for general transcription factor function and the specificity of gene-specific transcription activator protein function. If such factors were testis-specific, they would be expected to regulate patterns of gene expression that are important in the endocrine, spermatogenic and other functions of this organ. The present invention satisfies a need in the art for new compositions for polynucleotide sequences and encoded polypeptide products, immunological reagents and other derived materials in terms of providing unique reagents for the detection of defects in testis function such as idiopathic male infertility or other syndromes, for detection of dysfunctional patterns of gene expression and as reagents that can modulate gene expression.

SUMMARY OF THE INVENTION

The present invention includes DNA sequences that encode two structurally distinct isoforms of the human general transcription factor TFIIA α/β. One of these sequences is denoted as ALF, for TFIIA α/β-like factor, which is expressed predominantly in human testis. The second sequence contains ALF connected to a unique upstream sequence and is denoted as SALF, for Stoned B/TFIIA α/β-like factor. The present invention is also direct to recombinant polypeptide products and other derived materials. The uses of the invention include, but are not necessarily limited to, the propagation and preparation of the ALF and SALF DNA, RNA and recombinant proteins, and use of these materials as reagents and markers to detect and/or modify the function of eukaryotic cells in normal and disease states.

The present invention may be used in the detection of the endogenous ALF and SALF RNAs in eukaryotic cells using hybridization, polymerase chain reactions, immunological analysis and other methods. The invention may also be used along with the endogenous ALF and SALF DNAs, RNAs and proteins as specific in vivo pharmacological targets to artificially modulate the expression of eukaryotic genes. Furthermore, the ALF, SALF and the variable carboxyl terminal end may be introduced in a normal or modified versions of the ALF and SALF genes for expression in eukaryotic cells in order to replace or augment endogenous transcription factor activities (gene therapy). The present invention may also be used as testis-specific antigens for contraceptive vaccine development.

The present invention, in a general and overall sense, concerns the isolation and characterization of a novel transcription factor gene, ALF and carboxy terminal variable region. One embodiment of the present invention is a purified nucleic acid segment that encodes a protein having an amino acid sequence as shown in FIG. 2, in accordance with SEQ ID NO.: 2. Another embodiment of the present invention is a purified nucleic acid segment, further defined as including a nucleotide sequence in accordance with SEQ ID NO.: 1.

The present invention also concerns the isolation and characterization of a novel transcription factor gene, SALF and a carboxy terminal variable region. One embodiment of the present invention is a purified nucleic acid segment that encodes a protein having an amino acid sequence as shown in FIG. 3, in accordance with SEQ ID NO.:4. Another embodiment of the present invention is a purified nucleic acid segment, further defined as including a nucleotide sequence in accordance with SEQ ID NO.: 3. The 3' variable region that ALF and SALF have in common is encoded by the nucleic acid segment in accordance with SEQ ID NO.: 5 and expressed as an amino acid sequence as shown in SEQ ID NO.: 6.

In one embodiment the purified nucleic acid segment includes the nucleotide sequence of SEQ ID NOS.: 1, 3 and 5. As used herein, the term "nucleic acid segment" and "DNA segment" are used interchangeably and refer to a DNA molecule that has been isolated free of total genomic DNA of a particular species. Therefore, a "purfied" DNA or nucleic acid segment as used herein, refers to a DNA segment that includes novel transcription factor genes, ALF, SALF and a carboxy terminal variable coding sequence, yet is isolated away from, or purified free from, total genomic DNA, for example, total cDNA or human genomic DNA. Included within the term "DNA segment", are DNA segments and smaller fragments of such segments and recombinant vectors, including, for example, plasmids, cosmids, phage, viruses and the like.

Similarly, a DNA segment encoding an isolated or purified novel transcription factor genes, ALF, SALF, and a carboxy terminal variable coding sequence, gene refers to a DNA segment including ALF, SALF and a carboxy terminal variable coding sequence isolated substantially away from other rally occurring genes or protein encoding sequences. In this respect, the term "gene" is used for simplicity to refer to a protein, polypeptide or peptide encoding unit. As will be understood by those in the art, this functional term includes genomic sequences, cDNA sequences or combinations thereof. "Isolated substantially away from other coding sequences" means that the gene of interest, in this case ALF, SALF and a carboxy terminal variable coding sequence, forms the significant part of the coding region of the DNA segment. Of course, this refers to the DNA segment as originally isolated and does not exclude genes or coding regions later added by the hand of man to the segment.

In particular embodiments, the invention concerns isolated DNA segments and recombinant vectors incorporating DNA sequences that encode novel transcription factor genes, ALF, SALF and a carboxy teal variable coding sequence genes, and that include within the amino acid sequence an amino acid sequence in accordance with SEQ ID NO.: 2. Moreover, in other particular embodiments, the invention concerns isolated DNA segments and recombinant vectors incorporating DNA sequences that encode a gene which includes within its amino acid sequence the amino acid sequence of a ALF, SALF and a carboxy terminal variable coding sequence.

Another embodiment of the present invention is a purified nucleic acid segment that encodes proteins in accordance with SEQ ID NOS.:2, 4 and 6, further defined as a recombinant vectors. As used herein the term, "recombinant vector", refers to a vector that has been modified to contain a nucleic acid segment that encodes ALF, SALF, or the carboxy terminal variable coding sequence protein, or a fragment thereof. The recombinant vector may be further defined as an expression vector that includes a promoter operatively linked to the ALF, SALF, or the ALF/SALF variants having the carboxy terminal variable coding sequence encoding a nucleic acid segment.

A further embodiment of the present invention is a host cell, made recombinant with a recombinant vector including ALF, or SALF, and if present, a carboxy terminal variable coding sequence. The recombinant host cell may be a prokaryotic cell. In a one embodiment, the recombinant host cell is a eukaryotic cell. As used herein, the term "engineered" or "recombinant" cell is intended to refer to a cell into which a recombinant gene, such as a gene encoding ALF, SALF, or the carboxy terminal variable coding sequence, has been introduced. Therefore, engineered cells are distinguishable from naturally occurring cells which do not contain a recombinantly introduced gene. Engineered cells are thus cells having a gene or genes introduced through the hand of man. Recombinantly introduced genes will either be in the form of a cDNA, a copy of a genomic gene, or will include genes positioned adjacent to a promoter not naturally associated with the particular introduced gene.

It may be more convenient, however, to employ as the recombinant gene a cDNA version of the gene. One advantage of working with cDNAs is that the size of the gene is generally smaller and more readily employed to introduce into or "transfect" the targeted cell than will a genomic gene; typically an order of magnitude larger than cDNA gene. Alternatively, a genomic version of a particular gene may be used where desired.

In certain embodiments, the invention concerns isolated DNA segments and recombinant vectors that encode a protein or peptide which includes within its amino acid sequence an amino acid sequence essentially as set forth in SEQ ID NOS.:2, 4 or 6. Naturally, where the DNA segment or vector encodes a full length ALF or SALF protein, or is intended for use in expressing the sequences will be as essentially as set forth in SEQ ID NOS.:2, 4 and 6.

The term "a sequence essentially as set forth in SEQ ID NO.:2" means that the sequence substantially corresponds to a portion of SEQ ID NO.:2 and has relatively few amino acids which are not identical to, or a biologically functional equivalent of, the amino acids of SEQ ID NO.:2. Likewise the phrase is equally applied to SEQ ID NOS.: 4 and 6. The term "biologically functional equivalent" is well understood in the art and is further defined in detail herein as a gene having a sequence essentially as set forth in SEQ ID NOS.:2, 4 or 6, and that is associated with RNA transcription. Accordingly, sequences that have between about 70% and about 80%; or between about 81% and about 90%; or even between about 91% and about 99%; of amino acids that are identical or functionally equivalent to the amino acids of SEQ ID NOS.:2, 4 or 6.

In certain other embodiments, the invention concerns isolated DNA segments and recombinant vectors that include within their sequence a nucleic acid sequence essentially as set forth in SEQ ID NOS.:1, 3 or 5. The term "essentially as set forth in SEQ ID NO.: 1," is used in the same sense as described above and means that the nucleic acid sequence substantially corresponds to a portion of SEQ ID NO.:1, and has relatively few codons that are not identical, or functionally equivalent, to the codons of SEQ ID NO.:1. Likewise the phrase is equally applied to SEQ ID NOS.:3 and 5. The functionally equivalent codons are known in the art.

It will also be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region or may include various internal sequences, i.e., introns, which are known to occur within genes.

Excepting intronic or flanking regions, and allowing for the degeneracy of the genetic code, sequences that have between about 70% and about 80%; or between about 80% and about 90%; or between about 90% and about 99%; of nucleotides that are identical to the nucleotides of SEQ ID NOS.:1, 3 or 5 will be sequences that are "essentially as" the respective SEQ ID NOS. Sequences that are essentially the same as those set forth in SEQ ID NOS.:1, 3 or 5 may also be functionally defined as sequences that are capable of hybridizing to a nucleic acid segment containing the complement of SEQ ID NO.:1 under relatively stringent conditions. Suitable relatively stringent hybridization conditions will be well known to those of skill in the art and are clearly set forth herein, for example conditions for use with southern and northern blot analysis as described herein.

Naturally, the present invention also encompasses DNA segments that are complementary, or essentially complementary, to the sequence set forth in SEQ ID NOS.:1, 3 or 5. The nucleic acid segments of the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably. A nucleic acid fragment of almost any length may be employed, with the total length being limited by the ease of preparation and use in the intended recombinant DNA protocol. For example, nucleic acid fragments may be prepared that include a short stretch complementary to SEQ ID NOS.:1, 3 or 5, such as about 10 to 15 or 20, 30, or 40 or so nucleotides, and which are up to 10,000 or 5,000 base pairs in length, with segments of 3,000 being used in certain cases. DNA segments with total lengths of about 1,000, 500, 200, 100 and about 50 base pairs in length are also useful.

Another embodiment of the present invention is a nucleic acid segment that includes at least a 14-nucleotide long stretch that corresponds to, or is complementary to, the nucleic acid sequence of SEQ ID NOS.:1, 3 or 5. In one embodiment the nucleic acid is further defined as including at least a 20, 30, 50, 100, 200, 500, 1000, or at least a 3824 nucleotide long stretch that corresponds to, or is complementary with, the nucleic acid sequence of SEQ ID NOS.:1, 3 or 5. The nucleic acid segment may be further defined as having the nucleic acid sequence of SEQ ID NOS.:1, 3 or 5.

A related embodiment of the present invention is a nucleic acid segment that includes at least a 14-nucleotide long stretch that corresponds to, or is complementary with, the nucleic acid sequence of SEQ ID NO.:1 or 3, further defined as including a nucleic acid fragment of up to 10,000 base pairs in length. Another embodiment is a nucleic acid fragment including from 14 nucleotides of SEQ ID NO.:1 or 3 up to 5,000, 3,000, 1,000, 500 or 100 base pairs in length.

Naturally, it will also be understood that this invention is not limited to the particular nucleic acid and amino acid sequences of SEQ ID NOS.:2, 4 and 6. Recombinant vectors and isolated DNA segments may therefore variously include the ALF, SALF and variable region coding regions themselves, coding regions bearing selected alterations or modifications in the basic coding region, or they may encode larger polypeptides that nevertheless include ALF, SALF or variable region-coding segments or may encode biologically functional equivalent proteins or peptides that have variant amino acids sequences.

The DNA segments of the present invention encompass biologically functional equivalent ALF, SALF and variable region peptides. Such sequences may arise as a consequence of codon redundancy and functional equivalency that are known to occur naturally. Alternatively, functionally equivalent proteins or peptides may be created via the application of recombinant DNA technology, where changes in the protein structure may be engineered, based on considerations of the properties of the amino acids being exchanged. Changes designed by man may be introduced through the application of site directed mutagenesis techniques, e.g., to introduce improvements to the antigenicity of the ALF, SALF or variable region mutants in order to examine transcriptional activity or determine the presence of ALF, SALF or variable region protein in various cells and tissues at the molecular level.

Another embodiment of the present invention is a purified composition comprising a polypeptide having an amino acid sequence in accordance with SEQ ID NOS.: 2, 4 or 2 or 4 with 6. The term "purified" as used herein, refers to a transcription factor protein composition, wherein the ALF, SALF or ALF and SALF having the variable region proteins are purified to any degree relative to its naturally-obtainable state, i.e., in this case, relative to its purity within a eukaryotic cell extract, or a testis sample. A cell for the isolation of ALF, SALF or variants thereof is a cell of testicular origin, however, these proteins may also be isolated from patient specimens, recombinant cells, tissues, isolated subpopulations of tissues, and the like, as will be known to those of skill in the art, in light of the present disclosure. Purified ALF, SALF or variants thereof also refer to polypeptides having the amino acid sequence of SEQ ID NOS.: 2, 4, 2 and 6 or 4 and 6, free from the environment in which it may naturally occur. One may also prepare fusion proteins and peptides, e.g., where the ALF, SALF or variable portion coding regions are aligned within the same expression unit with other proteins or peptides having desired functions, such as for purification or immunodetection purposes (e.g., proteins that may be purified by affinity chromatography and enzyme label coding regions, respectively).

Turning to the expression of ALF, SALF and variable genes whether from cDNA or genomic DNA, protein may be prepared using an expression system to make recombinant preparations of ALF, SALF and variable genes proteins. The engineering of DNA segment(s) for expression in a prokaryotic or eukaryotic system may be performed by techniques generally known to those of skill in recombinant expression. For example, ALF, SALF and variable genes-GST (glutathione-S-transferase) fusion proteins are a convenient means of producing protein in a bacterial expression. Virtually any expression system may be employed in the expression of ALF, SALF and variable gene products. Eukaryotic expression systems, however, may also be used.

Transformation of host cells with DNA segments encoding ALF, SALF and variable genes also provides a convenient means for obtaining a protein for ALF, SALF and ALF or SALF including the variable portions. Complementary DNA (cDNA), genomic sequences and combinations thereof, are suitable for eukaryotic expression, as the host cell will, of course, process the genomic transcripts to yield functional mRNA for translation into protein.

Another embodiment is a method of preparing a protein composition comprising growing recombinant host cell comprising a vector that encodes a protein that includes an amino acid sequence in accordance with SEQ ID NOS.:2, 4 or 6, under conditions permitting nucleic acid expression and protein production followed by recovering the protein so produced. The host cell, conditions permitting nucleic acid expression, protein production and recovery, will be known to those of skill in the art, in light of the present disclosure of the ALF, SALF and variable region genes.

BRIEF DESCRIPTION OF THE DRAWINGS

For a more complete understanding of the features and advantages of the present invention, reference is now made to the detailed description of the invention along with the accompanying figures which corresponding numerals in the different figures refer to the corresponding parts and in which:

FIG. 1 depicts the cDNA sequence of ALF (SEQ ID NO.: 1);

FIG. 2 depicts the corresponding deduced amino acid sequence of ALF (SEQ ID NO.: 2), standard one-letter abbreviations for amino acids is used;

FIG. 3 depicts the cDNA sequence of SALF (SEQ ID NO.: 3);

FIG. 4 depicts the corresponding deduced amino acid sequence of ALF (SEQ ID) NO.: 4), standard one-letter abbreviations for amino acids is used;

FIG. 5 depicts the cDNA sequence of an alternative 3'-coding and untranslated region for both ALF and SALF (SEQ ID NO.: 5);

FIG. 6 depicts the corresponding deduced amino acid sequence of ALF (SEQ ID NO.: 6), standard one-letter abbreviations for amino acids is used;

FIGS. 7A and 7B depicts the schematic structures of the ALF and SALF cDNA sequences. FIG. 7A, The SALF cDNA sequence includes TFIIAα/β-like sequences and an upstream Stoned β-like region and is shown with selected restriction enzyme sites. FIG. 7B, The ALF cDNA sequence consists of TFIIAα/β-like sequences. The 5'-end of ALF was identified using gene-specific primers 2a2–20 and 2a2–22 and library-specific primers AP1 and AP2. The resulting clone, pRACE22, is shown as a single line. A PCR product that spans the entire ALF sequence (pRACE17) was obtained using gene-specific primer 2a2–17 and library-specific primer AP1. FIG. 7C, PCR products from SALF are amplified and visualized from human placenta and liver cDNA libraries. The primers used are indicated above each lane (2a2–1, 2a2–6 and 2a2–8). Lanes 5 and 6 are control reactions to which no cDNA template was added;

FIG. 10A through 10B are Northern blot analysis autoradiographs of ALF, TFIIAα/β and TFIIAγ transcripts. Poly (A) mRNA from various human tissues were probed with various gene-specific probes. A, ALF; B, 5'-SALF; C, TFIIAα/β; D, TFIIAγ; and E, actin.

FIGS. 11A through 11F are RNA dot blot analyses autoradiographs of ALF, TFIIAα/β and TFIIAγ transcripts; A single dot blot containing poly(A) mRNA from multiple human tissues is probed with A, ALF, B, 5'-SALF, C, TFIIAα/β, D, TFIIAγ; and E, a ubiquitin control. The source of the mRNA for each spot is listed in F, dashes indicate positions that do not contain mRNA.

FIGS. 12A through 12D show expression and functional analysis of ALF and SALF polypeptides. A, Coomassie-stained SDS-PAGE gel shows that the recombinant histidine-tagged ALF protein migrates at 69 kD) (lane 2) and that the recombinant rat TFIIAα/β and TFIIAγ proteins used in these studies migrate at 55 kD and 12 kD, respectively (lanes 3 and 4). B, p69 (ALF) can substitute for (TFIIAα/β) p55 in stabilizing the interaction between TBP and the Adenovirus Major Late promoter TATA element (−40 to −16). Additions to each reaction are listed above each lane. Polyclonal antiserum against human p55 is added to reactions in lanes 8 (2 $\mu$l), 9 (4 $\mu$l) and 10 (4 $\mu$l). C, Addition of p69 (ALF) and p12 (TFIIAγ) restore activity to transcriptionally inactive TFIIA-depleted HeLa nuclear extracts. Control (undepleted) and TFIIA-depleted extracts are indicated by a "C" and "D", respectively. D, A T7-promoter driven SALF construct produces an [35S]-labeled protein of approximately 170 kD in in vitro transcription-translation reactions.

DETAILED DESCRIPTION OF THE INVENTION

Figure 8A:
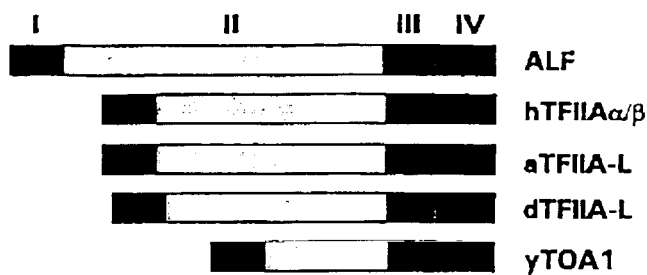
FIGS. 8A and 8B are schematic diagrams showing alignments of ALF and SALF sequences with related genes. A, ALF contains conserved regions I, III and IV and an internal nonconserved region II. Beneath ALF are diagrams of TFIIA large subunits from human (hTFIIAα/β), *Arabidopsis* (aTFIIA-L), *Drosophila* (dTFIIA-L) and yeast (yTOAI). B, A diagram of the N-terminus of SALF is shown, indicating an upstream serine, threonine, a proline-rich domain and a downstream domain that is homologous to *Drosophila* Stoned β and the clathrin APs $\mu$1 (AP47) and $\mu$2 (AP50) proteins.

While the making and using of various embodiments of the present invention are discussed in detail below, it should be appreciated that the present invention provides many applicable inventive concepts which can be embodied in a wide variety of specific contexts. The specific embodiments discussed herein are merely illustrative of specific ways to make and use the invention and do not delimit the scope of the invention.

Human transcription factor IIA (TFIIA) is a cellular factor that, together with additional protein components, regulates the expression of human genes. TFIIA is composed of proteins produced from two nucleic acid sequences (genes), one called hTFIIA α/β and the other hTFIIA γ (U.S. Pat. No. 5,652,117). These factors are expressed in human tissues and are thought to function primarily through interactions with the TATA-binding protein (TBP), a universally-required eukaryotic protein that functions at promoter DNA sequences to regulate gene expression.

In addition to the DNA sequences themselves, the functionality of the recombinant polypeptides produced from the ALF DNA sequences is shown using several biochemical assays. First, in conjunction with a recombinant TFIIAγ polypeptide, the recombinant ALF protein overproduced and purified from E. coli, can interact with recombinant human TATA binding protein to stabilize interactions on promoter DNA. Second, in conjunction with a recombinant TFIIAγ polypeptide, the recombinant ALF polypeptide can restore RNA polymerase II transcription activity to nuclear extracts from human cells that have been depleted of TFIIA. Related, antibody reagents raised against the recombinant ALF polypeptides react with the corresponding overproduced polypeptides suggesting that immunological detection of the endogenous protein(s) will be feasible. These studies substantiate the prediction that the ALF protein has a role in the regulation of human gene expression.

DEFINITIONS

As used throughout the present specification the following abbreviations are used; TF, transcription factor; TBP, TATA binding protein; ORF, open reading frame, EST, expressed sequence tag; kb, kilobase (pairs); UTR, untranslated region; kD, kilodalton; nt, nucleotide; aa, amino acids; bp, base pairs; PCR, polymerase chain reaction; AP, adaptor protein; DTT, dithiothreitol; PMSF, phenylmethylsulfonyl flouride; EDTA, ethylenediaminetetraacetic acid; IPTG, isopropyl β-D-thiogalactoside; AdML, Adenovirus Major Late; ALF, TFIIAα/β-like factor; SALF, Stoned B/TFIIAα/β-like factor.

Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not limit the invention, except as outlined in the claims.

The term "ALF" (TFIIAα/β-like factor) refers to the nucleotides essentially as set forth (SEQ ID NO. 1) or amino acid sequences essentially as set forth (SEQ ID NO.: 2). The term "SALF" (Stoned B/TFIIAα/β-like factor) refers to the nucleotides essentially as set forth (SEQ ID NO.: 3) or amino acid sequence essentially as set forth (SEQ ID NO.: 4). The term "alternative carboxy terminal domain" refers to nucleotide essentially as set forth (SEQ ID NO.: 5) and amino acid sequences essentially as set forth (SEQ ID NO.: 6) It is to be understood that alternative carboxy terminal sequence is present as an alternative 3'-coding and untranslated region that can be found on some ALF or SALF transcripts or cDNAs and is meant to be included or implied in all references to the term "ALF and SALF"; without referring to this alternative sequence explicitly each time.

The terms "a sequence essentially as set forth in SEQ ID NO.: (#)", "a sequence similar to", "nucleotide sequence" and similar terms, with respect to nucleotides, refers to sequences that substantially correspond to any portion of the sequences in SEQ ID NOS.: 1, 3 and 5. These terms refer to synthetic as well as naturally-derived molecules and includes sequences that possess biologically, immunologically, experimentally, or otherwise functionally equivalent activity, for instance with respect to hybridization by nucleic acid segments, or the ability to encode all or portions of ALF or SALF activities. Naturally, these terms are meant to include information in such a sequence as specified by its linear order.

The terms "a sequence essentially as set forth in SEQ ID NO.: (#)", "a sequence similar to", "amino acid sequence" and similar terms, with respect to mino acids, refers to peptides, polypeptides, proteins, fragments, fusions, derivatives and alterations thereof that substantially correspond to any portion of the sequences in SEQ ID NOS.: 2, 4 and 6. These terms refer to synthetic as well as naturally-derived molecules and includes sequences that possess biologically, immunologically, experimentally, or otherwise functionally equivalent activities, for instance, segments of amino acids which possess immunological activity as an antigenic determinant. Naturally, these terms are meant to include information in such a sequence as specified by its linear order.

The term "homology" and "similarity" refers to the extent to which two nucleic acids are complementary. The term "gene" is used to refer to a functional protein, polypeptide, or peptide encoding unit. As will be understood by those in the art, this functional term includes both genomic sequences, cDNA sequences, or fragments or combinations thereof, as well as gene products, including those that may have been altered by the hand of man.

The term "biologically equivalent" or "functionally equivalent" are understood in the art and is further defined herein as sequences that are interchangeable or similarly useful with reference to a given property, for instance selectivity of hybridization, or which encode amino acid segments that have similar properties.

The term "vector" refers to DNA or RNA sequences that have been modified to contain a nucleic acid segment that encodes ALF or SALF, or a fragment thereof. The vector may be further defined as one designed to propagate ALF and SALF sequences, or as an expression vector that includes a promoter operatively linked to the ALF or SALF sequences, or one designed to cause such a promoter to be introduced. The vector may exist in a state independent of the host cell chromosome, or may be integrated into the host cell chromosome.

The term "host cell" refers to cells that have been engineered to contain nucleic acid segments from ALF or SALF, or altered segments, whether archeal, prokaryotic, or eukaryotic. Thus, engineered, or recombinant cells, are distinguishable from naturally occurring cells that do not contain recombinantly introduced genes through the hand of man.

The term "agonist" refers to a molecule that enhances either the strength or the time of an effect of ALF or SALF and encompasses small molecules, proteins, nucleic acids, carbohydrates, lipids, or other compounds. The term "antagonist" refers to a molecule that decreases either the strength or the time of an effect of ALF or SALF and encompasses small molecules, proteins, nucleic, acids, carbohydrates, lipids, or other compounds.

The term "altered" or "alterations", or "modified" with reference to nucleic acid or polypeptide sequences is meant to include changes such as insertions, deletions, substitutions, fusions with related or unrelated sequences, such as might occur by the hand of man, or those that may occur naturally such as polymorphisms, alleles and other structural types. Alterations encompass genomic DNA and RNA sequences that may differ with respect to their hybridization properties using a given hybridization probe. Alterations of polynucleotide sequences that encode ALF or SALF, or fragments thereof, include those that increase, decrease, or have no effect on functionality. Alterations of polypeptides refer to those that have been changed by recombinant DNA engineering, chemical, or biochemical modifications, such as amino acid derivatives or conjugates, or post-translational modifications.

The term "antibody" refers to any of a class of immunological molecules with the capacity to interact specifically with one or more epitopes of ALF or SALF and includes those that have been altered or modified, for example, 'humanized' antibodies.

The term "complementary" refers to polynucleotide sequence that may form stable base pairs with another sequence under a given set of conditions. For instance a complementary strand refers to a sequence that is a sequence of nucleotides whose composition is dictated by the Watson-Crick base pairs (A-T, G-C). This term also refers to any polynucleotide sequence that can selectively interact with another under either permissive or stringent hybridization conditions, as known to those skilled in the art and, in this respect, includes sequences of DNA or oligonucleotides, RNA, protein nucleic acid, other nucleic acid derivatives and fragments thereof, which can reliably detect a particular sequence with a specificity that is useful for genetic or diagnostic studies.

The term "modulate" refers to the ability to effect a change in the structure, function, or regulation of ALF or SALF genes or gene products. These include methods for altering ALF or SALF gene activity and protein function.

The terms "segment", "fragment", "portion", "part", "region", or "domain", refers to any subsections, regardless of length, of nucleotide or amino acid sequences set forth in this invention that are either whole or which have been divided either naturally or by the hand of man.

The term "oligonucleotide probes" or "oligonucleotide primer" refers to a polynucleotide sequence between approximately 6 nucleotides to 70 to 80 nucleotides, but typically between 15–30 nucleotides, that can be used in direct hybridization, including microarray techniques, or in amplification assays to achieve a substantially selective detection of a complementary sequence. Such sequences are used for a wide variety of additional purposes, the basis of which is the relatively selective annealing to a particular target complementary nucleic acid sequence.

The term "sample" refers to any biochemical or biological specimen that is typically being analyzed for some property, for instance biological or biochemical activity of ALF or SALF, presence or absence of ALF or SALF protein, nucleic acid, including any alteration in the normal distribution or structure of these genes or encoded products. Samples may include, but are not limited to, cells and cell extracts or extracts thereof, including protein and membrane fractions, chromosomes, genomic DNA, RNA, cDNA and so forth, regardless of the particular state of isolation.

The term "stringent hybridization conditions" refers to an setting in which two polynucleotide sequences are hybridized under conditions that favor specific over nonspecific interactions. For instance, stringent hybridization conditions might include combinations of salt, organic reagents, blocking agents, detergents, temperature and so forth that allow for hybridization between highly similar sequences, such as those related by 95% or greater identity over a length of sequence sufficient for stable hybridization. The term "hybridization" also refers to complementary interactions between a polynucleotide sequence and an oligonucleotide, and may be performed under conditions of varying stringency that would be dictated by length and homology of the oligonucleotide(s) used and would be determined by one skilled in the art without undue experimentation.

The term "permissive hybridization conditions" refers to an setting in which two polynucleotide sequences are hybridized under conditions in that polynucleotide sequences with less similarity, for instance as low as 50–60%, are caused to interact. For instance, permissive hybridization conditions might include combinations of salt, organic reagents, blocking agents, detergents, temperature, and so forth that allow for stable hybridization, but may allow a greater degree of nonspecific, or background, hybridization than would be observed under stringent conditions. Hybridization between less related sequences is also facilitated by the use of nucleotides such as inosine within hybridizing nucleic acid segments.

The term "transformation" refers to any means by which DNA or RNA is caused to enter a recipient, or host, chromosome, cell, or organism.

The term "detection" refers to the ability to selectively detect a particular biological or biochemical compound. Detection of polynucleotide sequences in a sample, or the levels of such sequences in a sample, is often achieved by hybridization with a complementary polynucleotide or oligonucleotide sequence, or by amplification. Detection of polypeptides is often achieved on the basis of immunological recognition with antigen specific antibodies. Detection of biological or biochemical activity is often achieved by assaying a sample for an activity that is possessed by the compound being assayed.

The term "amplification" refers to the production of multiple copies of a given polynucleotide sequence. Amplification can be achieved as the growth of a vector contained within a host cell. Alternatively, the amplification of specific DNA, or reverse transcribed RNA, sequences that lie between two oligonucleotide primers can be achieved through the polymerase chain reaction, as known in the art.

The term "purified" or "isolated" with reference to DNA or other nucleic acid segment, or amino acid segment, refers to a sequence that includes novel transcription factor genes ALF and SALF, yet is isolated substantially away from, or purified substantially away from total genomic DNA, total cDNA, total or poly(A) RNA, total cellular, subcellular, or tissue extract, or other populations of molecules.

The term "ligand" refers to any molecule, whether nucleic acid, amino acid, or other chemical compositions that interacts with ALF or SALF.

INTRODUCTION

The synthesis of accurately-initiated messenger RNA in eukaryotic organisms requires the assembly of RNA polymerase II and the general transcription factors (TFIIA, B, D, E, F and H) at core promoters (1, 2). Human TFIIA is composed of 35 (a), 19 (b) and 12 (g) kD subunits encoded by the hTFIIAα/β(3, 4) and hTFIIAγ (5–7) (U.S. Pat. No. 5,652,117) cDNAs and evolutionarily conserved cDNAs have been characterized in yeast (yTOA1 and yTOA2) (8) and *Drosophila* (dTFIIA-L and dTFIIA-S) (9–11). The human TFIIA subunits are expressed in all or most human tissues and are though to function primarily through interactions with the TATA-binding protein (TBP), a universally required eukaryotic protein that functions a promoter sequences to facilitate and regulate gene expression.

TFIIA has multiple roles in transcription initiation by RNA polymerase II. First, TFIIA stabilizes the TBP-TATA element interaction (14–17). TFIIA also stimulates transcription by displacing TBP-associated repressors such as Dr1/NC2, Dr2/Topo1, HMG1 and DSP1 (18–22) and counteracts the ability of ADI/MOT1, hTAFII172, yTAFII145 and hTAFII250 to inhibit TBP binding to DNA (23–27). Second, TFIIA serves as a cofactor for the AP-1, Gal4-AH, Zta, VP16, CTF, NTF and Sp1 activators (4–7, 10, 28–31) and for the PC4 and HMG-2 coactivators (32, 33). Third, TFIIA is required for the isomerization and extension of TFIID-promoter contacts (34, 35) and for stabilizing interactions between TFIID and initiator sequences (36).

One of the nucleic acid sequences disclosed herein is called SALF (Stoned B/TFIIAα/β-like factor). SALF is composed of both Stoned B/clathrin AP-like and TFIIAα/β-like sequences. An initial incomplete SALF sequence was recognized in NCBI database queries using TFIIAα/β sequence query by the inventor as an expressed sequence tag (EST) DNA sequence (ID 259637) described by the I.M.A.G.E. consortium (37). Characterization and isolation of additional sequences by the inventor has revealed a composite 3,853 bp cDNA sequence (FIG. 3) that contains a 114 nucleotide 5'-UTR and a 161 nucleotide 3'-UTR with a poly(A) addition signal and a 29 nucleotide poly(A) tract. The deduced ORF commences with a putative start codon (AAGATGT) that is preceded by an in-frame stop codon 27 nucleotides upstream and predicts a 1,182-residue polypeptide (FIG. 4) with a molecular weight of 132 kD and pI of 5.1.

Another new DNA sequence described herein is called ALF, for TFIIAα/β-like factor. ALF is isolated by PCR from a human testis cDNA library and is described as a 1,617 bp cDNA (FIG. 1) that predicts a 478 amino acid polypeptide (FIG. 2) with a molecular weight of 52 kD and pI of 4.4. ALF contains a 15 nt UTR, a putative initiation codon (GTCATGG) that conforms to the Kozak consensus (A/G NNATGG) (38) and 17 bp downstream of the ATG that predict six amino acids (ACLNPV) not present in SALF. ALF is expressed predominantly, if not exclusively, in testis (FIG. 10A). Two additional new sequences that contain partial ALF-like sequences connected at nucleotide 1,344 to an alternative 261 bp 3'-end (FIG. 5) are identified (I.M.A.G.E. Consortium CloneIDs 785133 and 1657721). These sequences predict a C-terminus in which the last 35 amino acids of ALF are replaced with the residues "AFPRRTSFNT" (FIG. 6) followed by a stop codon and a 3'-UTR that contains a poly(A) addition signal and a poly(A) tail. PCR analysis has verified that both ALF and SALF cDNAs which contain this alternative 3'-end are present and can be PCR amplified, from human cDNA libraries. Importantly, none of the sequences disclosed herein have been previously reported, except as partial I.M.A.G.E. Consortium ESTs and as products of the inventor's work as currently disclosed and their intact sequences, structures, functions, uses and other characteristics.

Figure 8B:
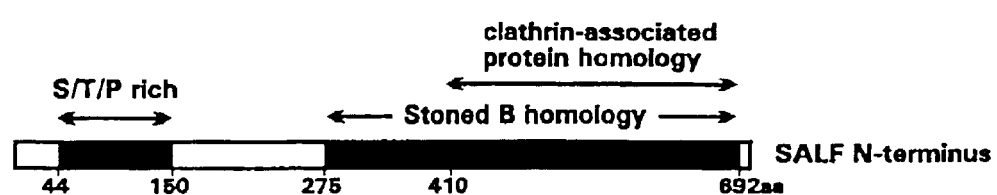

A schematic comparison of ALF and other TFIIA large subunit sequences from human (3, 4), *Drosophila* (9), *Arabidopsis* (Genbank Accession number X98861) and yeast (8) is shown in FIG. 5A. These sequences share a common organization consisting of conserved regions I and IV, acidic region III and an internal nonconserved region II. ALF is similar to its human TFIIAα/β counterpart in region I (aa 1–54; 67%) and region IV (aa 417–478; 73%) and in the negatively-charged region III (aa ~340–414; 42% D/E residues). In contrast, region II shares no homology with the corresponding region in hTFIIAα/β (or other TFIIA large subunits) and is approximately 100 residues longer. The unique N-terminus of SALF is 711 amino acids in length (FIG. 8B) and contains a region between amino acids 44 to 150 that is rich in proline (20%), serine (21%) and threonine (9%) residues. Residues between 275 and 692 display 47% similarity to the *Drosophila* Stoned B protein (39) and 46% similarity to an uncharacterized Stoned β-like ORF in *C. elegans*, C27H6.1 (53). The *Drosophila* stoned locus was first identified as a class of mutations that caused neurological defects such as temperature-sensitive paralysis (41) and it has been suggested that Stoned B functions in membrane trafficking in neurons (39). In addition, residues from 410 to 692 within the Stoned B-homology region are 33% and 37% similar to the mouse $\mu 1$ (AP47) and rat $\mu 2$(AP50) clathrin APs, respectively (FIG. 7B) (42, 43). The $\mu 1$ (AP47) and $\mu 2$ (AP50) clathrin APs are subunits of the AP-1 and AP-2 complexes associated with the trans-Golgi and plasma membranes, respectively and function in the internalization, sorting and recycling of receptors and other membrane proteins (44, 45). Thus, the N-terminus of SALF is related to a family of proteins involved in membrane trafficking.

ALF and SALF Genes

One aspect of the present invention is the polynucleotide sequences essentially as set forth as SEQ ID NOS.: 1, 3 and 5, and in FIGS. 1 and 3, the complement of these sequences, the RNA versions of both DNA strands and the information otherwise contained within the linear sequence of these polynucleotide sequences and fragments thereof. In the case of nucleic acid segments, sequences for use with the present invention are those that have greater than about 50 to 60% homology with any portion of the polynucleotide sequences described herein, sequences that have between about 61% and about 70%; sequences that have between about 71 and about 80%; or between about 81% and about 90%; or between 91% and about 99%; or which contain nucleotides that are identical, functionality equivalent, or functionally irrelevant, with respect to the nucleotides present in SEQ ID NOS.: 1, 3 and 5 are considered to be essentially similar. Also encompassed within the present invention are nucleic acids that encode polypeptides that are at least 40% identical or similar to the amino acid sequences shown in SEQ ID NOS.: 2, 4 and 6, and in FIGS. 2, 4 and 6.

The invention also encompasses other nucleic acids or nucleic acid like molecules that are sufficient in any regard to mimic, substitute for, or interfere with the ALF or SALF polynucleotide sequences or fragments thereof. It will also be understood that the nucleic acid and amino acid sequences may include additional residues, such as additional 5'- or 3'-sequences, and yet still be essentially as set forth in one of the sequences disclosed herein, so long as the sequence meets the criteria set forth, including the maintenance of functionality, or for the purpose of engineering altered functionality with respect to ALF and SALF.

Included within the invention are DNA or RNA segments including oligonucleotides, polynucleotides and fragments thereof, including DNA or RNA or nucleic acid-like sequences of genomic or synthetic origin, single or double stranded. The invention includes nucleic acid molecules, or nucleic acid-like molecules that are able to hybridize to the sequences in SEQ ID NOS.: 1, 3 and 5, under stringent or under permissive hybridization conditions, or to the complement of said sequences.

The invention also includes olignucleotide, or oligonucleotide-like sequences such as phosphothioates, or peptide nucleic acid sequences, that possess sufficient similarity with the sequences disclosed herein such that they are able to stably hybridize to the disclosed sequences, or their complements. Such sequences may be intended as antisense regulators of gene expression, or for the selective amplification or extension of adjoining sequences, for instance by PCR using a given annealing temperature, as would be determined by someone skilled in the art.

In addition to the sequences disclosed here, related sequences in other organisms, or homologs, will be readily identified by hybridization using the present sequences. This will facilitate the development of animal models for understanding disorders related to the overexpression, underexpression, or expression of forms with altered functionality, with respect to ALF, SALF, and similar sequences. Thus, related genes, and related mRNA transcripts, can be identified by one skilled in the art. The invention thus encompasses methods for the use of the disclosed sequences in various screening procedures aimed at isolating such species. For instance, colony or plaque hybridization techniques can be performed using radiolabeled sequences as a probe to detect complementary sequences in genomic and cDNA libraries.

Hybridization conditions with respect to temperature, formamide and salt concentrations, in such studies are chosen by one skilled in the art and vary with respect to the organism from which sequences are being isolated, and the sequence similarity, or lack thereof, that is expected based on evolutionary distances. Similar techniques will apply to the isolation of the genomic sequences that encode ALF and SALF, as well as those that encode related genes from organisms other than humans. Reference is particularly made to flanking regions, including upstream sequences that encode the core promoter and regulatory regions, as well as downstream regions, introns and intron/exon boundaries. Similar techniques will also apply to the identification of mutant alleles, polymorphisms, deletions, insertions, and so forth, in genomic and cDNA sequences. These may occur within the ALF and SALF sequences themselves, or may occur in regulatory regions, introns, intron/exon boundaries, or may reflect various insertions, partial or whole gene deletions, or substitutions, any of which may affect biological activity of a gene and gene product. In the case of humans, the identification of interindividual genomic differences in the ALF and SALF genes will be useful in diagnostic determinations.

Whole or partial sequences referred to above may also be identified and isolated using techniques that involve annealing of short oligonucleotides to complementary sequences, such as those as might be present in the genomic DNA of a particular organism, or in genomic or cDNA, including expression cDNA, libraries. Thus, PCR is used to obtain DNA sequences homologous to, and which lie between, two primers, usually between 15 to 30 nucleotides which have annealing temperatures typically between 60–80 degrees Celsius may be substantially purified. The choice of primer sequences, annealing conditions (temperature), number of amplification cycles, choice of polymerase, and so forth would be within the knowledge of one skilled in the art. Amplification assays will be generally applicable to the identification of sequences homologous to ALF and SALF, to the identification of flanking genomic or cDNA sequences, to the identification of mutated alleles, and so forth, in a manner that lends itself to rapid diagnostics.

Variations in PCR technology are also relevant, such as reverse transcriptase mediated PCR, in which mRNA or total RNA is reverse transcribed typically with an oligo dT or gene specific primer prior to PCR amplification. Techniques are also available which utilize only one gene-specific primer, together with a linker or adapter primer as may be present in a vector or attached to the ends of the DNAs to be amplified. For instance, the Genome Walker (Clontech) technique allows the isolation of genomic DNA that flanks a given oligonucleotide primer. Thus, the invention provides a method to isolate the testis-specific ALF gene promoter that can be used to drive cell- or tissue-specific expression of unrelated genes. Techniques are also available in which altered oligonucleotides are employed to generate specific mutations, deletions, insertions, or fusions in the disclosed sequences, or fragments thereof, for instance site directed mutagenesis.

Likewise, the current invention provides methods to map particular regions of a chromosome, and to identify and isolate homologous regions in artificial chromosomes, such as YACs, PACs, single chromosome libraries, and so forth. The current invention also provides techniques such as in situ hybridization in order to map disease-associated genes or other chromosomal markers, as well as mutations such as polymorphisms, inversion, translocations, deletions, insertions, and the like, which may be associated with particular health conditions.

Naturally, it will be understood that this invention is not limited to the particular nucleic acid sequences presented herein. Recombinant vectors, including for example plasmids, phage, viruses, and other sequences, and isolated DNA or RNA segments may therefore variously include the ALF and SALF sequences or their complements, and coding regions, as well as those that may bear selected alterations or modifications that nevertheless include ALF or SALF segments or may encode biologically or experimentally relevant amino acid sequences. Such sequences may be created by the application of recombinant DNA technology, where changes are engineered based on the consideration of the nucleotides or amino acids being exchanged, deleted, inserted, fused, or otherwise modified.

Likewise, the current invention encompasses sequences that may be naturally present as extensions of, or insertions within, the sequences disclosed herein, including alternative or longer 5' or 3' mRNA sequences, or intronic and promoter genomic sequences, or allelic or polymorphic versions of a gene. Similarly, natural, artificial, or synthetic fusions of ALF and SALF, and fragments thereof, with unrelated nucleic acids or amino acids such as those that encode epitope tags, binding proteins, marker proteins, and other amino acid sequences are included.

ALF and SALF Proteins and Polypeptides

One aspect of the invention is the protein, polypeptide, oligopeptide, or amino acid sequences or fragments thereof, of ALF and SALF, essentially as set forth in SEQ ID NOS.: 2, 4 and 6. Sequences that have greater than about 40–50% homology with any portion of the amino acid sequences described herein, sequences that have between about 51% and about 60%; sequences that have between about 61% and about 70% sequences that have between about 70 and about 80%; or between about 81% and about 90%; or between 91% and about 99%; or those that contain amino acids that are identical, functionally equivalent, or functionally irrelevant, for instance those specified by conservative, evolutionarily conserved, and degenerate substitutions, with respect to the amino acid sequences presented in SEQ ID NOS.: 2, 4 and 6 are included. The invention thus applies to ALE and SALF sequences, or fragments thereof, and nucleic acids which encode such polypeptides, such as those of other species. Reference is particularly, but not exclusively, made to the conserved N- (amino acids 1–54) and C-terminal (amino acids 417–478) regions of ALF and SALF, in contrast to similarity throughout the entire length. The invention thus encompasses amino acid sequences, or amino acid-like molecules, that are sufficient in any regard to mimic, substitute for, or interfere with the ALF or SALF amino acid sequences, or fragments thereof.

The invention encompasses ALF and SALF amino acid sequences that have been altered in any form, either through the use of recombinant engineering, or through post-translational or chemical modifications, including those that may be produced by natural, biological, artificial, or chemical methods. Naturally, it will be understood that this invention is not limited to the particular amino acid sequences presented herein. Altered amino acid sequences include those which have been created by the application of recombinant technology such that specific residues, regions, or domains have been altered, and which may be functionally identical, or which may possess unique biological or experimental properties with regards to function or interactions with natural and artificial ligands.

For instance such modifications may confer longer or shorter half-life, reduced or increased sensitivity to ligands that modify function, ability to detect or purify polypeptides, solubility, and so forth. Alternatively, such sequences may be shorter oligopeptides that possess an antigenic determinant, or property that interferes, or competes, with the function of a larger polypeptide, for instance sequences similar to the functionally important and conserved N- and C-terminal domains, and those that affect interactions between TFIIA subunits and other proteins. Such sequences may be created by the application of the nucleotides or amino acids being exchanged, deleted, inserted, fused, or otherwise modified. Likewise, the current invention within, the sequences that may be naturally present as extensions of, or insertions within, the sequences disclosed herein, including alternative or longer N- and C-terminal sequences, or alternatively spliced protein isoforms.

Production and purification of polypeptides may be achieved in any of a variety of expression systems known to those skilled in the art, including recombinant DNA techniques, genetic recombination, and chemical synthesis. For instance, expression in prokaryotic cells may be achieved by placing protein coding nucleic sequences downstream of a promoter, such as T7, T3, lacI, lacZ, trp, or other cellular, viral, or artificially modified promoters including those that may be inducible by IPTG, tetracycline, maltose, and so forth. Such promoters are often provided for in commercially available recombinant DNA vectors such as pRSET ABC, pBluescript, pKK223-3, and others, or are easily constructed to achieve such a purpose, and often include the presence of multiple cloning sites (MCS) to facilitate typically contain efficient ribosome binding sites, and in some cases transcription termination signals.

Cells for the expression of such proteins are normally *E. coli*, but could include *B. subtilus*, *Streptomyces* or others prokaryotes. The incorporation of such recombinant DNA can be efficiently achieved by calcium chloride transformation, electroporation, and so forth. In the case of *E. coli*, cells typically grow in LB media with an appropriate antibiotic selection, for instance ampicillin, chloramphenicol, tetracycline and so forth in order to retain the recombinant vector, although vectors which integrate into the cellular chromosome are also possible. The promoter of many recombinant expression vectors require induction by an inducer compound, for instance IPTG, to facilitate high levels of transcription initiation and subsequent protein production. In some instances, nucleic acid sequences within the coding region may be altered to suit the codon usage patterns of a gives model expression system or organism.

Peptides, oligopeptides and polypeptides may also be produced by chemical synthesis, for instance solid phase techniques, either manually or under automated control such as Applied Biosystems 431 peptide synthesizer (Perkin Elmer). After synthesis, such molecules are often further purified by preparative high performance liquid chromatography. Thus, the invention provides methods for the production of epitopes for antibody production, or the production of small molecules that enhance or interfere with a specific function or interaction of the ALF or SALF polypeptides.

Methods to produce and purify said polypeptides in eukaryotic systems are widely available and understood by those proficient in the art. Cells for such production are known to include yeast and other fungi, *Drosophila* and Sf9 cells, cells of other higher eukaryotic organisms such as HeLa, COS, CHO and others, as well as plant cells. Similarly, expression could be achieved in prokaryotic or eukaryotic extracts that are able to translate RNAs into proteins, such as rabbit reticulocyte lysates.

Vectors for expression in such systems are widely availably both commercially or can be prepared. Such vectors typically are driven by promoters derived from cellular or viral genes, such as CMV, HSV, EBV, HSV, SV40, Adenovirus, LTRs, vaccinia, baculovirus polyhedrin promoter, CaMV, TMV, Rubisco, and so forth, and could obviously include the promoters for the ALF or SALF genes themselves. Such vectors are often designed be regulated by the presence of enhancer or other regulatory element sequences. Introduction of such vectors into cells is often achieved by calcium phosphate or DEAE dextran technologies, liposome mediated techniques, electroporation, or viral mediated infection. Maintenance of such vectors may be achieved by selectable marker such as that conferred by HSV thymidine kinase, HGPRTase, herbicide resistance, visible markers, and so forth.

Selection of an appropriate methodology would be within the scope of those skilled in such methodologies, using the current invention, and would include any combination of host cell and vector which can achieve desired production goals. For instance, the ability of a host cell to drive efficient full-length polypeptide production, glycosylation, membrane anchoring, secretion, absence of contaminating mammalian proteins or infectious agents, proteolytic processing, lipid modification, phosphorylation and so forth may dictate the use of baculovirus/insect cell systems, mammalian cells systems, plant cell systems and so on. In the case of in vitro translation extracts, one embodiment is the coupled transcription and translation of a nonreplicable recombinant vector, where translation is often visualized by the incorporation of a radiolabeled amino acid. The system selected may further depend on the desirability of obtaining purified polypeptides for further characterization, on whether the intent is to evaluate the effect of the overexpressed proteins on cellular gene expression, in vivo or in vitro, to identify compounds that enhance or interfere with the function of the overexpressed polypeptides, or other purposes.

For stable, long term expression, integration within the host cell chromosome, or as an autonomously replicating element, may be used. ALF or SALF genes, including defective (knock-out) genes themselves, can also be introduced to produce transgenic animals, for instance rodents, primates, insects, and other organisms. These methods provide an opportunity to develop and study animal models for specific gene defects, or for augmented expression of certain genes. Such techniques include pronuclear microinjection, retrovirus mediated transfer and other viral vectors, gene targeting into embryonic stem cells, homologous or nonhomologous recombination and electroporation. The presence and expression of transgenes may occur in all or some cells of a given organism. Likewise, expression of the transgene may be constitutive or inducible and may occur in all or only some cell types. Characterization of the introduced transgene, or mutant (knock-out) construct is typically achieved by genomic Southern blotting and/or PCR analysis of genomic DNA, and its expression by RNA—RNA, DNA-RNA, DNA—DNA hybridization such as Northern analysis, or by RT-PCR analysis.

The invention also relates to cells which contain such recombinant constructs, where the host cell refers to mammalian, plant, yeast, insect, or other eukaryotic cells, or to prokaryotic, or archae, and vectors that are designed for a given host. Promoter-vector combinations could be chosen by a person skilled in these arts. In some cases, the desired outcome may not be protein, but RNA, and recombinant vectors would include those with inserts present in either forward or reverse orientations.

Many of the vectors and hosts have specific features that facilitate expression or subsequent purification. For instance DNA sequences to be expressed as proteins often appear as fusion with unrelated sequences that encode polyhistidine tags, or HA, FLAG, myc and other epitope tags for immunochemical purification and detection, or phosphorylation sites, or protease recognition sites, or additional protein domains such as glutathione S-transferase (GST), maltose binding protein (MBP), and so forth which facilitate purification. Vectors may also be designed which contain elements for polyadenylation, splicing and termination, such that incorporation of naturally occuring genomic DNA sequences that contain introns and exons can be produced and processed, or such that unrelated introns and other regulatory signals require RNA processing prior to production of mature, translatable RNAs. Proteins produced in the systems described above could be subject to a variety of post-translational modifications, such as glycosylation, phosphorylation, nonspecific or specific proteolysis or processing.

Purification of ALF, SALF, or carboxy terminal variants produces as described above can be achieved by any of several widely available methods. Cells may be subject to freeze-thaw cycles or sonication to achieve disruption, or may be fractionated into subcellular components such as nuclear and cytoplasmic fractions prior to further purification. Purification may be achieved by one or more techniques such as precipitation with salts or organic solvents, ion exchange, hydrophobic interaction, HPLC and FPLC chromatograpic techniques. Affinity chromatographic techniques could include the use of polyclonal or monoclonal antibodies raised against the expressed polypeptide, or antibodies raised against or available for an epitopic tag such as HA or FLAG. Similarly, purification can be aided by affinity chromatography using fusions to the desired proteins such as GSH-affinity resin, maltose affinity resin, carbohydrate (lectin) affinity resin or, in a one embodiment, Ni-affinity resin, and so forth. In some instances purification is achieved in the presence of denaturing agents such as urea or guanidine, and subsequent dialysis techniques may be required to restore functionality, if desired.

Antibodies to ALF and SALF Proteins

The current invention encompasses antibodies of any class, such as IgA, IgD, IgE, IgG, IgM, and subclasses, including polyclonal, monoclonal, chimeric, single chain, humanized and antibody fragments, including synthetic antibodies as in recombinant antibody expression library, single chain antibodies, anti-idiotype antibodies and other immunological, or binding, factors that recognize one or more epitopes of the ALF and SALF proteins. Such reagents as derived from ALF and SALF provide methods for detection and purification of ALF and SALF polypeptides, including endogenous, recombinant, or synthetic factors, and as a means to affect changes in gene expression or other functions by immunochemically targeting ALF or SALF. Proteins, polypeptides, oligopeptides, or peptides will be suitable for the production of monoclonal and/or polyclonal antibodies against the ALF, SALF, and alternative C-terminal regions, and for the use as standards or controls in assays such as ELISA, RIA, FACS, Western analysis, and so forth.

Antigens used to generate antibody reagents have a length of at least five amino acids, and in some cases 10 or more, up to the length of the full-length protein. Techniques that are used to obtain such reagents are described in, e.g., Harlow, et al., Antibodies: A laboratory Manual, Cold Spring Harbor Laboratories, New York (1988). For polyclonal antibodies, animals such as rabbits, mice, rats, goats, and so forth are injected with up to several hundred micrograms of antigen together with an adjuvant such as Freund's, either complete or incomplete, followed by a series of booster injections. Blood (serum) collected at intervals following injections are tested for antibody titer and specificity. Use of such antibodies is often facilitated by further purification by salt fractionation, antigen affinity chromatography, or other purification methods, to obtain more pure, and thus more specific, antibodies.

Monoclonal antibody production can be achieved by several methods, including the hybridoma technique, the human B-cell hybridoma technique and the EBV-mediated hybridoma technique. Thus, in one embodiment, antibody producing cells from mice spleen are fused with myeloma cells. Hybrids are then subcloned and screened for antibodies with the antigen, in this case ALF, SALF, the alternative C-terminal domain, or related antigenic fragments. Antibodies against related polypeptides which are intended for the same purpose constitute an included methodology for detection.

Humanized antibodies are those in which the antigen recognition region from an antibody with a given specificity that possess domains from human antibodies so as not to be recognized or rejected by humans. Chimeric antibodies are those in which genes for the antigen recognition region and the constant regions are spliced from different organisms, for instance mouse and human.

In another embodiment, ALF or SALF antigens may be used to generate an immunological reaction, as described above, which generates an immunological response that, in turn, causes a biological or developmental effect, such as modulation of gene expression, or which affects a cellular process such as testis function or spermatogenesis.

Detection or Diagnosis of ALF or SALF Genes, Gene Products and Abnormalities thereof One embodiment of the invention is the use of the invention for the detection of DNA and RNA sequences of ALF, SALF and the alternative carboxy terminus. Such efforts might be directed towards evaluating the levels of these polynucleotides, to evaluate whether such sequences are present or absent in given individuals, or to evaluate whether corresponding sequences in given individuals are in some way absent, abnormal, or otherwise altered. Thus, the invention encompasses methods and reagents for the production and use of oligonucleotide probes, or DNA or RNA probes of various lengths, that have sufficient similarity to ALF and SALF nucleic acids to allow for selective detection. Methods for labeling could employ radioactive nucleotides, e.g., using T4 polynucleotide kinase, DNA polymerases, in vitro synthesis of RNA probes, PCR amplification of labeled DNAs, as well as nonradioactive techniques such as incorporation and detection of fluorescent, chromogenic, chemiluminescent compounds, as well as avidin/biotin based systems.

Other detection methods could include those based on direct hybridization, such as include fluorescent in situ hybridization (FISH), in situ hybridization, DNA "chip", or "microarray" hybridization technology, Southern and Northern hybridization analysis, RNA dot blot hybridization, dipstick, pin, dot blot, in situ PCR, and other techniques. Others methods may be based on annealing between short typically 15–30 nucleotide, complementary DNA or RNAs followed by enzymatic extension, such as PCR analysis of genomic DNA or cDNA, reverse-transcriptase mediated PCR using RNA. Such oligonucleotides are derived from the sequences in SEQ ID NOS.: 1, 3, or 5, or their complements, or from flanking 5'- or 3' cDNA or genomic regions, or from introns or alternatively spliced exons, alleles, promoter or enhancer regions, and so forth. Visualization of the results from such methods is accomplished by a number of methods, including light or fluorescent microscopy, autoradiographic detection, or detection based on ethidium bromide stained agarose gels, DNA sequencing, and so forth. These and other techniques would be those available to and recognized by those skilled in the art.

To provide a basis to establish whether gene structure or expression correlates with a given pathology, results between normal and experimental subjects are compared with respect to the sizes of hybridizing bands, nucleic acid sequence differences, quantitative differences in gene copy number and expression. Thus standard values from normal individuals are compared to those from individuals which display a particular set of symptoms to determine if symptomatic individuals fall outside normal deviations. Such detection may be faciliated by ELISA, or microplate, type assays in which a chemical composition may be coupled to a support to facilitate reading of multiple samples rapidly, for instance in an automated format, as judged by some spectrophotometric or colorimetric response. Such techniques could also be used to assess the efficacy of other treatments related to the function or production of ALF or SALF genes and gene products. The ability to detect corresponding DNA or RNA sequences could be provided for in an appropriately licensed pharmaceutical kit that would contain sequence-specific reagents capable of selective detection. Such detection might be made with whole genomic DNA, for example from blood or other tissues, or from RNA or DNA obtained from cultured cells or sampled tissues, or using chromosomes of cells, as examples.

Comparison among samples derived from given individuals using a given detection methodology, for example differential hybridization, conformational polymorphisms, sequencing, and so forth would be compared to those from normal controls. Such procedures may be directed towards the detection of ALF, SALF, and alternative carboxy terminal sequences themselves, or to corresponding genomic sequences, including the promoter and intronic sequences, or to the lack of these sequences due to deletion. Detection procedures would enable differences in test samples, for example those which may be testis-derived, including those which may be dysfunctional or cancerous, to be compared with normal samples.

In one embodiment of the invention, a polynucleotide sequence derived from those disclosed herein is used as a target in a microarray as a means to identify the presence or absence of expression, the presence or absence of gene mutants, and so forth. For instance, an oligonucleotide, or oligonucleotides, are synthesized (typically between 6 and 70 or 80 nucleotides long) that are computer optimized for minimal secondary structure and minimal likelihood of nonspecific interactions. These oligonucleotides, or mixed sets of oligonucleotides, are then coupled to, or synthesized directly on a support, usually in a grid arrangement, such as nylon, glass, or other membrane, wafer, chip, slide, and so forth. Labeled probes from a biological sample may be either DNA, RNA, or reverse transcribed DNA, are used to hybridize to the microarray. After washing, the retention of the probe to a given oligonucleotide is typically determined by fluorescence analysis in a scanner. These techniques are be understood by one of skill in the art and performed in accordance with the appropriate instrumentation.

Alternatively, the invention provides a method for isolating identical or related genes from humans or other organisms that may have similar functionality, for instance by PCR or hybridization analysis of genomic and/or cDNA libraries. The invention also provides a means to identify the corresponding genomic DNA and the corresponding tissue-specific promoter DNA and regulatory sequences.

The present invention provides a means to use the ALF or SALF specific antibodies described above in the form of an appropriately licensed kit or pharmaceutical pack which contains reagents and supplies for detecting the expression of relevant polypeptides in cells and tissues. Such approaches include enzyme-linked immunosorbent assay (ELISA), radioimmunoassay (RIA), fluorescent activated cell sorting (FACS). Another approach is a Western blot, in which crude protein extracts are separated on SDS-PAGE gels, transferred to nitrocellulose and hybridized with a specific antibody. Hybridization typically involves prior blocking with nonspecific proteins and dilution of antibody to a level that facilitates specific as opposed to nonspecific interactions. Visualization typically occurs by the action of a secondary antibody which is typically coupled with a domain such as horse radish peroxidase or radiolabeled protein A which possesses an activity or property which can be visualized. Samples tested may be identical in size and abundance to those observed in normal samples, or they may be increased or decreased in abundance, or they may possess altered mobilities.

Likewise, the level of ALF and SALF antigen in a given sample may be evaluated through the use of an ELISA assay, in which samples are attached to a support, typically a set of plastic wells and are incubated with specific antibody. After washing, secondary antibodies are added that allow visualization, and indicate levels, of the primary antigen which are present. Controls, or standards, would consist of recombinant antigen present in a series of dilutions, as a standard curve. Plates are then read with a microplate spectrophotometer. Antibodies are also used for immunolocalization of antigenic proteins within tissues and cells, to determine appropriate expression and localization of antigen among various subcellular compartments. Antibodies may be employed in specific immunoprecipitation or immunopurification protocols that are designed to identify and isolate corresponding cellular antigens, or complexes that may contain such antigens. Differences among cells or tissues that may be causative with respect to abnormal biological function are identified in this way.

The invention also provides a means to identify endogenous levels of ALF and SALF activity. Tissue samples or biopsies are obtained and extracts of nuclear proteins or whole cell extracts are produced by homogenization in a physiological buffer together the presence of protease inhibitors, if necessary. Extracts are then tested directly for activity, for instance as described in the TBP-dependent bandshift assay. Alternatively, further precipitation or chromatograhic purification may sometimes be necessary to isolate and differentiate endogenous activities away from crude samples.

Identification of Ligands and Interaction Partners of ALF and SALF

The invention provides a method of identifying compounds, whether they be specific chemicals or drugs, polypeptide fragments of ALF, SALF or other proteins, in vitro or in vivo selected oligopeptides isolated by selections such as phage display, or RNA or DNA sequences that with affinity for such proteins and complexes. Such compounds are typically identified based on affinity-based interaction assays, or on their ability to modulate function in simple representative functional assays, for instance, modulation of TBP-TATA interactions as visualized by bandshift assays. Such compounds are typically next tested in an in vitro functional assay such as that described to test their ability to interfere with (antagonists), or facilitate (agonists), the function of RNA polymerase II, either in terms of basal or activated transcription. Such compounds may be tested in tissue-derived cells, or in cell lines for modulation of activity, for instance gene expression. Such compounds are then evaluated for their efficacy as therapeutic agents, particularly with respect to the modulation of gene expression in a tissue or organisms itself.

Thus, such compounds may be added individually, or in pools, to assess whether in the presence of the polypeptides, RNA polymerase II and other required general factors and upstream activators, and they can affect initiation and chain elongation of RNA from particular promoters, including those which may be tissue- or cell-type specific. For instance, compounds may be tested for their ability to modulate the expression of genes that require ALF or SALF function, as judged by visualization of a reporter such as beta-galactosidase, luciferase, G-free cassette, and so forth. Similarly, the invention provides a method to identify compounds that could confer could confer an activated phenotype, or a dominant negative phenotype, in terms of the polypeptides themselves. In particular, mutations are constructed according to site directed mutagenesis techniques or by random mutagenesis techniques that are known to practitioners of the art, and selected and evaluated for functionality. Further, computer modeling of the ALF or SALF polypeptdides, either based on X-ray crystallographic data, or on comparisons with known TFIIA structures provides a method to fit, or design, compounds that may interfere with various functions or interactions of ALF or SALF, for instance subunit—subunit interactions, subunit-TBP interactions, and so forth.

The method also provides for solid phase high throughput screening methods for identifying ligands which interact with ALF or SALF. For instance ALF or SALF, alone or with a TFIIAγ subunit, or even with TBP, promoter DNA, or other factors, are linked to a solid support. Compounds to be tested for interaction are co-incubated, washed to remove nonspecific or less specific interactions, and those that remain are of relatively higher affinity. Detection is achieved by any of a number of techniques, including antibody linked markers, radioisotopic counting and so forth, preferably via automated sample handling.

Identification of ligands may also be achieved using multiple rounds of PCR-mediated selection of high affinity nucleic acid ligands, in which interacting ligands are typically separated from non-interacting ligands by gel shift. Likewise, the promoter element sequences that have affinity for ALF or SALF containing complexes, for instance those which contain TFIIAγ and even TBP, can be selected for by multiple rounds of PCR amplification starting from either random or TATA-containing oligonucleotides. The derived sequences may be compared to the genomic DNA sequences, such as promoters.

Factors such a proteins, or small peptides that interact with ALF or SALF may be identified by phage display, in which a library of oligopeptides with diverse sequences are detected by virtue of their ability to be recognized or selectively retained by, ALF or SALF polypeptides that are labeled, or fixed to solid support. Interacting phage are detected, reamplified and reselected until single isolates, or plaques are obtained. The sequence of the interacting motif is identified by sequencing all or part of the coat protein which has been engineered to contain such sequences.

The invention also provides techniques to identify natural interacting proteins of ALF and SALF. For instance, immunoprecipitation using antibodies specific to ALF, or SALF, or to epitope tags that have been engineered within recombinant ALF or SALF nucleic acids, can be used to remove, or pull-down, ALF and SALF containing complexes from cellular extracts, for instance those derived from testis tissue or testis cell lines. Such techniques can be performed either in solution, or with the antibody linked to a solid support, such as a resin or a well.

Similarly, ALF or SALF with GST-encoding nucleic acids in the form of a recombinant expression vector allow overproduction and purification of the fusion protein. Such a protein may be bound to affinity resin such as S-hexyl glutathione, and cellular or recombinant proteins, or fragments thereof, can be tested for their ability to interact with ALF or SALF. Such an analysis typically involves comparisons of the bound proteins compared to eluted proteins using a resin that is loaded with the fusion protein and a resin that is loaded with the GST domain alone.

The yeast two-hybrid and related systems also provide methods to identify interacting factors. In this method, genetic fusions of DNA binding domains and activation domains are made separately to the target and bait polypeptides and clones that express interacting epitopes are identified based on a transcription activation assay in vivo. This may be performed in variety of cell types, including yeast and mammalian cells.

The invention provides a means to identify genes which may be selectively regulated by the ALF or SALF polypeptides. For instance, targets of ALF or SALF function may be identified in cells which are engineered to overexpress, or underexpress the ALF or SALF genes, or altered forms of these proteins. RNA isolated from such cells may be purified and compared to that present in normal cells. For instance, differential display, subtractive hybridization and microarray techniques are available to evaluate differences in gene expression, or RNAs, present in two or more populations. For use with microarray analysis, gene specific oligonucleotides or segments, typically 6 to 70 or 80 nucleotides are coupled to, or synthesized on, a solid support and mRNA populations (cDNA) are prepared from normal control cells or tissues and from cells or tissues which are either overexpressing ALF or SALF, or which contain knockouts in these genes. After hybridization and washing, the microarrays can be scanned for hybridization, for instance as registered by fluoresence. In this way genes whose expression is unaltered, decreased, or increased in response to the presence or absence of the transcription factors ALF or SALF can be identified.

Likewise, serial analysis of gene expression (SAGE) analysis provides a method in which short sequences derived from cDNAs from two populations of mRNA are quantitatively compared for their frequency of identification. The technique relies on the use of restriction enzymes that cut away from their binding site and the concatamerization of the resulting fragments into a vector for sequencing. Thus, single sequencing runs of each isolate can give data from multiple original cDNAs. Confirmation of the isolates is often achieved by Northern or quantitative or semi-quantitative PCR analysis. Thus, engineered ALF and SALF genes provide a method to identify additional genes that are "downstream" or regulated, by ALF or SALF, which may in turn be targets for detection, diagnosis and intervention with regard to correlating disease conditions.

Treatment of ALF- and SALF-Related Disorders

The invention provides methods for the isolation, detection, diagnosis, development of animal models, or therapeutic protocols applicable to any organism, such as cats, dogs, pigs, cows, horses, rabbits, birds, primates and humans. Thus, nucleic acid sequences, antibodies and other agonistic or antagonistic ligands may be used to inhibit or augment patterns of gene expression by modifying ALF and SALF function, or the function of the ALF or SALF genes themselves. Such compounds could be delivered in various media, including buffered saline or other carriers or solvents dependent on the chemical nature of the compound and the route of delivery. Delivery mechanisms could include intranasal, subcutaneous, intramuscular, intraperitoneal, intradermal, intravenous, topical, enteral, rectal, intramedullary, intraarterial, sublingual, or other means. Doses would vary depending on the need to alleviate or correct particular symptoms and on the particular agent. Standard measures of effectiveness and toxicity in cell cultures and animals are given by ED50, the dose that is therapeutic for 50% of the sample, and LD50, the dose that is lethal to 50% of the sample. Administration of polypeptides, drugs and other therapeutic compounds would be apparent to those skilled in the art with respect to the present teachings, and in accordance with licensing and regulatory requirements. Normal dosages range from 0.1 ug to 100 mg, up to a total dose of 1 g, depending on the particular formulation, delivery route, patient sensitivity, patient history, clearance rates, half-life, and other considerations as would be generally available to one skilled in the art. Compositions with high therapeutic indices will generally be used. Additional details are available in such references as Remington's Pharmaceutical Sciences. Initial estimates as to effective concentrations may be determined using cells grown in culture, or in animal models. The invention also provides for the use of proteins, agonists, antagonists, nucleic acid sequences and vectors administered in conjunction with other therapeutic agents, according to accepted usages by those skilled in the art.

Concentrations for delivery of nucleic acids, polypeptides, antibodies and transgenics will be specific to particular cells, conditions, etc. For instance, the invention provides methods for the use of oligonucleotides, phosphorothioate oligonucleotides, peptide nucleic acids and other nucleic acid-like, or nucleic acid binding molecules that could be administered in a manner and amount designed to treat the specific indications using antisense therapy. Such sequences may contain additional, or other modifications, such as methylation, acetylation, thiolation of normal bases, as well as the use of unconventional bases in order to enhance stability. Such complementary sequences are generally targeted along the coding or control regions of ALF or SALF, so as to control transcription or translation and may be supplied as a drug, or as an antisense transcript, or other functional molecule such as a ribozyme, derived from from a transgene.

Similarly, pharmaceutical intervention would also be applicable to specific antibodies and to other compounds that target ALF and SALF function. Therapeutic antibodies that recognize ALF or SALF may be used to directly target, and inactivate, ALF and SALF polypeptides through antibody-epitope interactions, possibly when coupled with compounds that facilitate cellular entry. Likewise, such antibodies may serve as a carrier or targeting molecule by which other therapeutic compounds might be brought to cells which harbor ALF or SALF.

Engineered Organisms and Animal Models

The present invention provides methods for the production of engineered cells and organisms such as rodents, but which may include humans or other organisms in need of therapy, that express ALF or SALF or altered forms in the form of a recombinantly introduced gene (transgene). For instance, cells can be engineered with polynucleotide sequences so that expression of active or dominant negative ALF or SALF polypeptides are produced, for instance to compensate for the loss, or overactivity, of such polypeptides in a patient. The current invention also provides methods for ex vivo gene therapy, in which recombinant vectors are introduced into stem cells, or other accessible cell population, and, after engineering and propagation, are transplanted back into the patient. Such engineered constructs might be designed to produce RNA that will be translated into ALF or SALF proteins, or altered versions thereof. Alternatively, such constructs might be designed to produce antisense RNA designed to inhibit transcription or translation, or to produce ribozymes that target ALF and SALF RNAs for degradation. Alternatively, the current invention also provides methods by which deletions, or knock-outs of the ALF or SALF genes can be produced, in order to establish animal models for pathological conditions that result from the absence of these genes.

These methods are known to those in the art, and may include stable integration of DNA sequences by recombination, adenoviral, retroviral and other means which are intended to introduce and propagate sequences in engineered cells, by techniques such as pronuclear microinjection, liposome mediated uptake, electroporation of embryos, homologous (targeted) recombination, and so forth. One embodiment is receptor-mediated gene transfer, whereby the transgene is coupled with a ligand via polylysine, where the ligand is some molecule that interacts selectively with surface molecules, or receptors, on a selective cell population such as those that might be present in testis, or an antibody that has specificity for a cell-specific surface marker.

Depending on the method chosen, the introduced gene might replicate autonomously as part of a vector, or may integrate a specific or random sites. Such a gene may be engineered so as to contain regulatory sequences that drive expression in a constitutive, inducible, tissue- or cell-cycle specific, or other manner, as desired. Another embodiment of the invention is the use of homologous recombination targeting vector that contains a recombinant ALF or SALF gene that has been engineered to be nonfunctional. Such a construct can be used replace the endogenous gene by homologous recombination, for instance, in embryonic stem ES cells from mice, followed by selection, implantation and development of the modified cells into adult organisms which contain targeted defects in ALF or SALF genes.

The presence of the transgene, or knockout construct, may be established by genomic blotting or genomic PCR, and its expression, or lack thereof, by Northern blotting or RT-PCR, or other hybridization technologies. Transgenes that express ALF or SALF proteins, or altered forms, can be further detected using antibodies specific for the expressed protein. Once transgenic founder animals are produced, they are bred to produce colonies of animals with particular genotypes, including inbreeding and outbreeding to develop homo- and heterozygous animals, with respect to the transgene, in different backgrounds. Cells derived from such animals may also be isolated and propagated for study. Further examination at the organismal, tissue, cellular, subcellular and biochemical levels will establish the biological effects of organisms that contain engineered ALF or SALF genes. Such organisms and cells will also provide assay systems with which to identify agonists and antagonists that may compensate for observed defects, and which may perform similar functions in other organisms, including humans.

The invention may be better understood with reference to the following examples. These examples, however, should not be taken to limit the scope of the invention in any way.

EXAMPLE 1

Cloning and Detection of ALF and SALF

The 5'-end of SALF was amplified by PCR (40 cycles) using 4 μl of the human placental cDNA library (Clonetech) with primer 2a2–6 (5'-AGTAACCCGAATGCTTAA-3') (SEQ ID NO.: 8) and a commercially available library-specific adapter primer AP1 (Clontech). The resulting products were reamplified (35 cycles) with primer 2a2–8 (5'ATGCTAGCTGAACCACGTG-3') (SEQ ID NO.: 9) and a commercially available nested library-specific adaptor primer AP2 (Clontech) used to obtain a 2,930 bp product, which was subcloned into the pCRII cloning vector (Invitrogen) to form pRACE4 (FIG. 7A). Sequence analysis of this and EST ID 256637 constitute SEQ ID NO.: 3. Human SALF cDNAs were identified by PCR amplification (35 cycles) of 1.1 and 0.9 kb products from human placenta, liver and testis "Marathon" cDNA libraries (Clontech) using 25 pmol of the upstream primer 2a2–1 (5'-AGAAATTCCCTCTGATTG-3') (SEQ ID NO.: 7) and the downstream primers 2a2–6 and 2a2–8. The 1.1 and 0.9 kb products derived from the liver cDNA library were subcloned into pGEM-T Easy (Promega). Supreme analysis of the liver-derived products shows that they are identical to those present in both SEQ ID NO.: 3. These products are diagrammed in FIG. 7A, and shown in FIG. 7C.

ALF sequences were isolated by PCR (35 cycles) using 4 μl of the human testis cDNA library (Clontech) with the gene-specific primer 2a2–20 (5'-CCAGAAGGTAGAATTGCGGGTTGCTGTAGC-3') (SEQ ID NO.: 12) and primer AP1 (Clontech), and reamplified with 2a2–22 (5'-GGAGTTTGAAGTGCCCAGGTCTGCTGTGG-3') (SEQ ID NO.: 19) and primer AP2 (Clontech). The 369 bp amplification product is subcloned into pGEM-T Easy (Promega) to form pRACE22. The resulting clone (pRACE22; FIG. 7B) contains 298 bp that are identical to SALF and 35 bp 5'-end that is unique to SEQ ID NO.: 1. A full-length ALF PCR product is amplified (35 cycles) from 4 ml of the testis cDNA library (Clontech) using primer 2a2–17 (5'-GGTGCTGTCATGGCCTGCCTCA-3') (SEQ ID NO.: 13), located within the unique 5'-end of ALF, and primer AP1 (Clontech). The resulting 1.7 bp fragment is subcloned into pGEM-T Easy to form pRACE17 (FIG. 7B). The sequence of the resulting clone is identical to the composite SALF sequence except for its unique 5'-end and a longer poly(A) tail (~90 nucleotides) which begins four nucleotides downstream of the poly(A) tail in SALF. The composite sequences of pRACE17 and pRACE22 are SEQ ID NO.: 1.

EXAMPLE 2

Detection of Genomic DNA Sequences that Encode ALF

Figure 9:
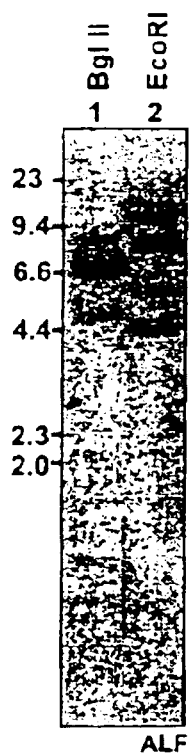
FIG. 9 shows human genomic DNA digested with either BglII or EcoRI and hybridized with an ALF probe. The enzymes are indicated above each lane (lanes 1 BglII; lanes 2, EcoRI). The positions of the molecular weight size markers are indicated to the left of each panel.

Genomic DNA (10 μg) from HeLa cells is digested with the indicated restriction enzymes (BglII and EcoRI), electrophoresed on 0.7% agarose gels using 1×TBE buffer, and transferred overnight to nitrocellulose membranes (Schleicher and Schuell). Hybridization is performed under stringent conditions at 42° C. in 50% formamide, or at 68° C., in hybridization buffer (6×SSC, 0.5% SDS, 5× Denhardt's solution, and 100 μg/ml salmon sperm DNA). The probe is a full-length NdeI-BamHI ALF fragment contained within the vector construct pRSET-ALF. The blot is washed at 65° C. in 0.1×SSC and 0.5% SDS, and exposed at −80° C. to XAR-5 film (Kodak). Hybridization with the ALF probe revealed bands of 8.6, 6.9, 5.0, and 1.0 kb (BglII; lane 1), or 11.5, 8.4, 6.0, and 4.5 kb (EcoRI; lane 2). These results (FIG. 9) show that sequences complementary to ALF are present and detectable in human genomic DNA.

EXAMPLE 3

Expression of ALF and other Human TFIIA Subunit mRNAS

Northern blots containing 2 ug of poly(A) mRNA from 16 human tissues are obtained from Clontech. Gene-specific probes for hybridization are as follows: ALF, a 621 bp NcoI-KpnI fragment or an 899 bp HincII-BglII fragment from region II (FIG. 7B); 5'-SALF, a 1,002 bp EcoRI—EcoRI fragment from pRACE4 containing the 5'-UTR and nucleotides encoding the first 282 residues (FIG. 7A); hTFIIAα/β, a full-length 1.1 kb EcoRI—EcoRI fragment from lambda11 or a 282 bp HaeIII-Hae III fragment from region II; hTFIIAγ, a full-length 355 bp NdeI-BamHI fragment or a 262 bp NdeI-EcoRI fragment from pRSEThp12; and actin controls (Clontech). DNA fragments were typically labeled with [α32P]-dCTP using Ready-to-Go DNA Labeling Beads (Pharmacia) and purified over NICK columns (Pharmacia). Northern blots are hybridized for 1 hour in ExpressHyb solution (Clontech) and washed at 68° C. for 1 hour. Membranes were typically exposed for 1–2 days to either XAR-5 film (Kodak) or a Phosphorimager screen (Molecular Dynamics). The results are shown in FIGS. 10A–10E.

Hybridization with a probe from the TFIIAα/β-like region of SALF reveals a 1.8 kb mRNA that is present in testis, but not in other tissues (FIG. 10A, lane 12). The isolation of the ALF cDNA which corresponds to this species is illustrated in FIG. 7B. The predicted 3.8 kb SALF mRNA is not visible in mRNA from any of the tissues examined, including placenta, liver, and testis from which SALF can be amplified by PCR (FIGS. 7A and C). These results indicate that ALF, and TFIIAα/β, are the major transcripts encoding human TFIIA large subunits, and that SALF is relatively rare. Hybridization with a probe specific for the 5'-end of SALF (5'-SALF) reveals a 6.5 kb species that is present at highest levels in heart, placenta, kidney, prostate, and uterus (FIG. 10B, lanes 1, 3, 7, 11, and 13) and at lower levels in other tissues. This transcript, termed RNA6.5, was not detected using the ALF-specific probe (FIG. 10A), indicating that it does not contain a downstream ALF domain. Thus, RNA6.5 is an independent human transcript that contains sequences similar, or identical, to those present at the 5'-end of SALF.

A dot blot purchased from Clontech containing 89–514 ng poly(A) mRNA from 50 adult and fetal tissues is hybridized as follows: [α32P]-dCTP-labeled DNA is combined with 30 μg Cot1 DNA (Boehringer-Mannheim) and 100 μg salmon sperm DNA, denatured, and allowed to renature in 200 ml of 5×SSC at 68° C. for 30 minutes prior to addition. After hybridization in 5 ml ExpressHyb solution at 65° C. overnight with the probe, the blot was washed in 0.1×SSC at 55° C. Membranes were exposed as follows: FIGS. 11A, 19 hours; 11B, 2 hours 45 minutes; 11C, 14 hours; 11D, 25 hours, and 11E, 30 minutes. For reprobing, Northern and dot blots were stripped twice with 0.5% SDS at 100° C., cooled to room temperature, and exposed overnight to confirm the loss of the previous signals. Quantitation of hybridization signals is performed using ImageQuaNT (Molecular Dynamics), and relative transcript levels in testis are determined by comparison to an average level from non-testis tissues. Ubiquitin (FIG. 11E) is a control provided by the manufacturer (Clontech).

Using an ALF-specific probe, a strong signal was observed in testis that is due to the presence of the 1.8 kb ALF transcript (FIG. 11A, position D1). In addition, weak signals were observed in approximately 24 of the remaining tissues, including small intestine, bladder, uterus, and prostate (positions E3, C5, C6, and C7). These signals indicate that ALF, or SALF, is expressed to low levels in non-testis tissues, and their detection in this study reflects the greater sensitivity of the dot blot. When this blot was stripped and reprobed with the 5'-SALF probe, signals were detected in all tissues (FIG. 11B), with highest levels in placenta, uterus, spinal cord, and fetal kidney (positions F4, C6, B7, and G3) and several others, and lower levels in the remaining tissues. Because this probe detected high levels of RNA6.5 (but not SALF) in Northern analysis, the signals in FIG. 6B are primarily due to the expression of RNA6.5.

Further inspection of the data reveals that the signals detected with the ALF-specific probe in FIG. 11A are present in a range of tissues that is nearly identical to those observed in FIG. 11B. This holds true for approximately 20 tissues, including bladder, uterus, prostate, ovary, placenta (positions C5, C6, C7, D2, and F4), and others, but not for testis (position D1). Likewise, the absence of signals in FIG. 6A correlates with the absence of signals in FIG. 11B. The results suggest a relationship between the expression of RNA6.5 with ALF-containing transcripts (possibly SALF) present at low levels in non-testis tissues. Hybridization with human TFIIAα/β and TFIIAγ-specific probes (FIGS. 11C and 11D) shows that the corresponding mRNAs are expressed in all tissues. Quantitation of the results confirms that ALF (50-fold), TFIIAα/β (4-fold), and TFIIAγ (10-fold) are enriched in testis tissue.

EXAMPLE 4

Production of ALF and SALF Polypeptides

To prepare recombinant ALF protein for functional assays, a 479 amino acid histidine-tagged polypeptide that spans residues Val7 to Trp478 was overexpressed and purified. Primers used in these studies had the corresponding sequences as follows: A1 (5'-ACTACTCATATGGCACACCATCACCAT-CACCATGTACCTAAACTCTACAGATC T-3') (SEQ ID NO.: 14) and A2 (5'-AGTAGTGGATCCTTACCACTCTGCATCACC-3') (SEQ ID NO.: 15) were used to create a 1,445 bp NdeI-BamHI PCR fragment whose reading frame begins with the N-terminal extension MHHHHHHV (SEQ ID NO.: 16) and terminates with the natural TAA stop codon. This construct does not encode the first six amino acids (MACLNP, SEQ ID NO.: 17) found in the intact testis-derived ALF cDNA. After subcloning into pRSETC (Invitrogen), the resulting construct (pRSET-ALF) was transformed into $E.$ $coli$BL21 (DE3)pLysS (Novagen) and was expressed and purified essentially as follows. Cells were grown in LB media at 37° C. to an $OD_{600}$ of ~0.5, and production of the 69 kD recombinant ALF protein is induced with 2 mM IPTG. Cells were harvested 3 hours post-induction, solubilized in Buffer A (0.1 M NaH2PO4, 0.01 M Tris pH 8.0, and either 6 M guanidine or 8 M urea), and sonicated five times for 30 seconds. The denatured cell lysate (~20 ml) was incubated with 2 ml Ni-NTA agarose resin (Qiagen) at room temperature for 1 hour. The resin was washed successively with Buffer A containing 8 M urea at pH 8.0, 6.3, and 5.9, and bound polypeptides are eluted at pH 3.5. Preparation of expression constructs for rat TFIIAα/β and rat TFIIAγ subunits (Genbank Accession numbers AF000943 and AF000944, respectively) and purification of the corresponding 55 and 12 kD recombinant proteins were performed. For transcription studies the recombinant p69 and p12 proteins were codialyzed in order to prevent precipitation of the p12 subunit.

The predicted size of this polypeptide is 53 kD, but the mobility on SDS-PAGE is 69 kD (FIG. 12A, lane 2). This observation is similar to results showing that the predicted 42 kD product of hTFIIAα/β migrates at 55 kD (3, 4), and may be due to the effect of charged region III. The mobilities of the purified recombinant rat TFIIAα/β (p55) and TFIIAγ (p12) subunits used in these studies are also shown in FIG. 12A (lanes 3 and 4). These polypeptides are at least 98% identical to their human counterparts.

A related procedure is used to prepare human TBP. Specifically, TBP was expressed in $E.$ $coli$ BL21(DE3)pLysS (Novagen) from a pET11d (Novagen) vector that contains a histidine tagged TBP open reading frame, induced with 2 mM IPTG at OD600 0.3 and purified at 4° C. from the soluble fraction of the bacterial lysate over Ni-NTA agarose. Purification was performed by washing the resin with D700 buffer (20 mM HEPES, 20% glycerol, 0.2 mM EDTA, 10 mM β-mercaptoethanol, 0.5 mM PMSF, and 700 mM KCl) that contained 5 mM, 10 mM and 15 mM imidazole, and eluting bound polypeptides with D700 buffer that contained 100 mM imidazole. Recombinant proteins were dialyzed against Buffer C (10 mM Tris pH 7.9, 2 mM DTT, 20% glycerol, and 0.5 mM PMSF) containing 100 mM KCl prior to use.

To express SALF in a rabbit reticulocyte lysate system, primers NN1 (5'-TACTGCTCGAGCAACTTTAGAGT-3') (SEQ ID NO.: 18) and 2a2–8 were used to generate a 2,988 bp product from pRACE4. An internal 2,207 bp XhoI-BglII fragment (aa 1–716) derived from this PCR product was then inserted into the XhoI-BglII digested pT7T3D vector that contains EST ID259637. Because an internal BglII—BglII fragment that spans aa 717–1,084 was excised during preparation of this vector, this fragment was later reinserted in the appropriate orientation to create a full-length SALF ORF (pT7T3-SALF). This construct (0.8 mg) was used to program rabbit reticulocyte lysates in the presence of [$^{35}$S]-methionine as described by the manufacturer (Promega). Labeled polypeptides are separated on 8% SDS-PAGE gels, and visualized by autoradiography. To determine whether this full-length SALF cDNA construct is capable of directing the translation of an intact protein, in vitro transcription-translation reactions were performed.

As shown in FIG. 12D, rabbit reticulocyte lysates programmed with pT7T3-SALF produced an [$^{35}$S]-methionine-labeled polypeptide that migrated at 170 kD (compared to a predicted size of 132 kD). Lysates programmed with pT7T3-SALF truncated at an internal EcoRI site at nucleotide position 960 produced a 36 kD product similar to the predicted size of 32 kD (data not shown). These results demonstrate that although SALF contains a suboptimal ATG initiation codon (AAGATGT) and encodes a large ORF composed of two distinct regions, it can be translated efficiently.

EXAMPLE 5

ALF is a Transcription Factor For RNA Polymerase II

Functionality of ALF was demonstrated in TBP-dependent mobility shift assays and in RNA polymerase independent in vitro transcription assays. Mobility shift assays were performed using 10 fmol of a [γ-$^{32}$P] ATP kinase-labeled TATA-containing an oligonucleotide that spans nucleotides −40 to −16 of the Adenovirus Major Late (AdML) promoter. Binding reactions (25 μl final volume) were performed in 10 mM HEPES (pH 7.9), 2% (wt/vol) PEG-8000, 60 mM KCl, 5 mM DTT, 0.2 mM EDTA, 5 mM ammonium sulfate, 4 mM MgCl$_2$, and 8% glycerol. Recombinant rat p55 (30 ng; 29 nM), rat p12 (1.1 ug; 3.5 uM), human ALF (180 ng; 137 nM) and human TBP (125 ng; 133 nM) were added to reactions as indicated. Reactions were incubated for 30 minutes at room temperature, and complexes are separated on native 5% polyacrylamide gels containing 0.5×TBE and 5% glycerol. Competition experiments contain either cold AdML TATA or SP1 oligonucleotides, and antibody supershift reactions contain 2–4 μl of rabbit polyclonal antiserum raised against the 55 kD hTFIIAα/β polypeptide (3).

The activity of polypeptides was tested in electrophoretic mobility shift assays under conditions in which TATA-Binding Protein (TBP) alone is unable to bind DNA (FIG. 12B, lane 1). The presence of TFIIAα/β(p55) and TFIIAγ (p12) stabilized the TBP-DNA interaction via TFIIAα/β/γ-TBP-DNA complex formation (lane 2). Likewise, the recombinant ALF (p69) polypeptide, in conjunction with the TFIIAγ (p12) subunit, was able to form ALF/γ-TBP-DNA complexes (lane 5). Formation of this complex depends on the presence of both ALF and TFIIAγ. Although ALF (p69) is 102 amino acids longer than TFIIAα/β (p55) and migrates as a larger species in SDS-PAGE, the ALF/γ-TBP-DNA complex migrates slightly faster than the TFIIAα/β/γ-TBP-DNA complex (lanes 2 and 5). These reactions are run side-by-side on the same gel using ALF and TFIIA subunits that have been purified and renatured using the same procedure. The specificity of ALF/γ-TBP-DNA complexes is similar to TFIIAα/β/γ-TBP-DNA complexes, as judged by competition with specific TATA (lanes 3 and 6) and non-specific Sp1-site (lanes 4 and 7) oligonucleotides. In addition, both complexes are supershifted to the well when co-incubated with antiserum against hTFIIAα/β (lanes 8 and 9), indicating that ALF and TFIIAα/β are immunologically related, and are present in the respective complexes.

To demonstrate that ALF is a functional polypeptide that regulates gene expression, TFIIA-dependent in vitro transcription assays are performed. For this purpose, advantage was taken of the fact that TFIIAα/β contains an intrinsic seven-histidine region that allows for the efficient removal of TFIIA from HeLa cell nuclear extracts using Ni-NTA agarose. In brief, 200 ul of extract were incubated with 100 μl Ni-NTA agarose resin for 30 minutes at 4 C in the presence of 400 mM KCl. Control extracts were processed similarly, except that no Ni-NTA agarose was present. After microcentrifugation for 5 minutes, the supernatants were removed and dialyzed for 3 hours against Buffer C that contains 100 mM KCl. Transcription reactions were performed using a template (pMLC2AT) that contains the AdML promoter upstream of a G-free cassette. The template was linearized at a SmaI site just beyond the G-free cassette prior to use. Each reaction (20 μl) contained: 8 μl nuclear extract (~60 μg protein), 2 μl (550 ng) of recombinant p69 (0.22 μM) and p12 (0.9 μM) proteins, 1 μg pMLC2AT, 10 mM HEPES (pH 7.5), 25 mM KCl, 6 mM MgCl2, 625 μM UTP, 625 μM ATP, 35 μM CTP, 200 μM O-methyl-GTP, 3% glycerol, 0.7 μl [α-32P] CTP and 37.3 units of RNAguard (Pharmacia). After incubation at 30° C. for 45 minutes, the reactions were terminated by adding 270 μl stop solution (0.25 M NaCl, 1% SDS, 20 mM Tris pH 7.5, 5 mM EDTA and 66.7 μg/ml tRNA) and extracted with an equal volume of 1:1 phenol/chloroform. Ethanol precipitated transcripts were resuspended in formamide-containing loading dye and electrophoresed on 5% acrylamide gels containing 1×TBE and 8 M urea. Depleted extracts were transcriptionally inactive, but were restored to normal activity by the addition of TFIIA As shown in FIG. 12C (lane 1), control (undepleted) extracts produce a [γ$^{32}$P]-CTP labeled G-free RNA transcript were expressed under the control of the AdML promoter (pMLC2AT). The addition of recombinant ALF (p69) and TFIIAγ (p12) to these extracts did not enhance transcription (lane 2). TFIIA-depleted extracts were transcriptionally inactive, and were not affected by the re-addition of either ALF (p69) or TFIIAγ (p12) alone (lanes 3–5). The addition of both ALF (p69) and TFIIAγ (p12), however, restored transcription to the level observed with control extracts (lane 6). The results of the electrophoretic mobility shift and in vitro transcription assays shown in FIGS. 12B and 12C, demonstrate that ALF has TFIIAα/β-like functional activity via TBP, and that both ALF and TFIIAα/β require TFIIAγ, or a functionally similar subunit, for activity.

While this invention has been described in reference to illustrative embodiments, this description is not intended to be construed in a limiting sense. Various modifications and combinations of the illustrative embodiments, as well as other embodiments of the invention, will be apparent to persons skilled in the art upon reference to the description. It is therefore intended that the appended claims encompass any such modifications or embodiments.

What is claimed is:

1. The isolated protein encoded by a polynucleotide comprising a nucleic acid sequence set forth in SEQ ID NO.: 1.

* * * * *

SEQUENCE LISTING

<160> NUMBER OF SEQ ID NOS: 18

<210> SEQ ID NO 1
<211> LENGTH: 1617
<212> TYPE: DNA
<213> ORGANISM: Homo sapien

<400> SEQUENCE: 1

```
gctggaggtg ctgtcatggc ctgcctcaac ccggtgccta aactctacag atctgtaatt      60
gaagatgtaa ttgaaggagt tcggaatcta tttgctgaag aaggtataga ggaacaagtt     120
ttaaaagact tgaagcagct ctgggaaacc aaggttttgc agtctaaagc aacagaagac     180
ttcttcagaa atagcatcca atcacctctg tttactcttc agttgccgca cagcttgcac     240
caaacattgc aatcgtcaac agcatcatta gttattcctg ctggtagaac tcttccaagt     300
tttaccacag cagaactggg cacttcaaac tccagtgcaa actttacttt tcctggttat     360
cccattcatg taccagcagg tgtgacacta cagactgtat ctggtcacct ttataaagtc     420
aatgtaccaa ttatggtgac agagacttct ggaagagcag gtattcttca gcatccaatt     480
cagcaagtat ttcaacagct tggccagcct tcagtaatac aaactagtgt tccacaattg     540
aatccatggt ctcttcaagc aactactgaa aaatcacaga gaattgaaac cgtgctacag     600
caacccgcaa ttctaccttc tgggccagta gataggaaac acttagaaaa tgccaccagt     660
gatatacttg tatctcctgg aaatgagcat aaaatcgtgc ctgaagcttt gttgtgtcat     720
caggaaagtt ctcactatat cagtcttcca ggtgttgtat tttctccaca ggtctctcaa     780
acaaattctg atgtggagtc agtgctcagt ggttcagcta gcatggctca aaatctgcat     840
gatgagtccc tctccacaag ccctcatggg gctctccacc agcacgtgac tgatattcag     900
cttcatattc ttaaaaatag gatgtatgga tgtgattctg taaagcaacc aagaaatata     960
gaggaaccca gcaacatacc tgtatcagag aaggattcta attctcaggt ggatttaagc    1020
attcgggtta ctgatgatga tattggtgaa ataattcaag tagatggaag cggtgataca    1080
tcttccaatg aagaaatagg aagtacaaga gatgcagatg agaatgaatt tctagggaat    1140
attgacgggg gagatctgaa ggtacctgaa gaagaagctg acagtatttc aaatgaggat    1200
tcagccacaa acagtagtga taatgaagac cctcaagtaa acattgtaga agaggaccct    1260
ttaaattctg gagatgatgt tagtgaacag gatgtgccag acctgtttga cacggataat    1320
gtaattgtct gtcagtatga taagattcat cgaagcaaga caaatggaa attctatttg    1380
aaagatggtg ttatgtgttt tggagggaga gactatgtat ttgcaaaagc cattggtgat    1440
gcagagtggt aaaccttgtg agctcagtac atctattttg tgaacatcag ttggactata    1500
ttgcatattg tgaattcatt tttattttga atatagtcca gcacagagct gttcaaattt    1560
ttagttcact gtatggaatt taataaaatt ataattcaga tgcagataca attacac       1617
```

<210> SEQ ID NO 2
<211> LENGTH: 478
<212> TYPE: PRT
<213> ORGANISM: Homo sapien

<400> SEQUENCE: 2

```
Met Ala Cys Leu Asn Pro Val Pro Lys Leu Tyr Arg Ser Val Ile Glu
 1               5                  10                  15
Asp Val Ile Glu Gly Val Arg Asn Leu Phe Ala Glu Glu Gly Ile Glu
            20                  25                  30
```

-continued

```
Glu Gln Val Leu Lys Asp Leu Lys Gln Leu Trp Glu Thr Lys Val Leu
            35                  40                  45

Gln Ser Lys Ala Thr Glu Asp Phe Phe Arg Asn Ser Ile Gln Ser Pro
        50                  55                  60

Leu Phe Thr Leu Gln Leu Pro His Ser Leu His Gln Thr Leu Gln Ser
65                  70                  75                  80

Ser Thr Ala Ser Leu Val Ile Pro Ala Gly Arg Thr Leu Pro Ser Phe
                85                  90                  95

Thr Thr Ala Glu Leu Gly Thr Ser Asn Ser Ser Ala Asn Phe Thr Phe
            100                 105                 110

Pro Gly Tyr Pro Ile His Val Pro Ala Gly Val Thr Leu Gln Thr Val
        115                 120                 125

Ser Gly His Leu Tyr Lys Val Asn Val Pro Ile Met Val Thr Glu Thr
        130                 135                 140

Ser Gly Arg Ala Gly Ile Leu Gln His Pro Ile Gln Gln Val Phe Gln
145                 150                 155                 160

Gln Leu Gly Gln Pro Ser Val Ile Gln Thr Ser Val Pro Gln Leu Asn
                165                 170                 175

Pro Trp Ser Leu Gln Ala Thr Thr Glu Lys Ser Gln Arg Ile Glu Thr
            180                 185                 190

Val Leu Gln Gln Pro Ala Ile Leu Pro Ser Gly Pro Val Asp Arg Lys
        195                 200                 205

His Leu Glu Asn Ala Thr Ser Asp Ile Leu Val Ser Pro Gly Asn Glu
        210                 215                 220

His Lys Ile Val Pro Glu Ala Leu Leu Cys His Gln Glu Ser Ser His
225                 230                 235                 240

Tyr Ile Ser Leu Pro Gly Val Val Phe Ser Pro Gln Val Ser Gln Thr
                245                 250                 255

Asn Ser Asp Val Glu Ser Val Leu Ser Gly Ser Ala Ser Met Ala Gln
            260                 265                 270

Asn Leu His Asp Glu Ser Leu Ser Thr Ser Pro His Gly Ala Leu His
        275                 280                 285

Gln His Val Thr Asp Ile Gln Leu His Ile Leu Lys Asn Arg Met Tyr
        290                 295                 300

Gly Cys Asp Ser Val Lys Gln Pro Arg Asn Ile Glu Glu Pro Ser Asn
305                 310                 315                 320

Ile Pro Val Ser Glu Lys Asp Ser Asn Ser Gln Val Asp Leu Ser Ile
                325                 330                 335

Arg Val Thr Asp Asp Ile Gly Glu Ile Thr Gln Val Asp Gly Ser
            340                 345                 350

Gly Asp Thr Ser Ser Asn Glu Glu Ile Gly Ser Thr Arg Asp Ala Asp
        355                 360                 365

Glu Asn Glu Phe Leu Gly Asn Ile Asp Gly Gly Asp Leu Lys Val Pro
        370                 375                 380

Glu Glu Glu Ala Asp Ser Ile Ser Asn Glu Asp Ser Ala Thr Asn Ser
385                 390                 395                 400

Ser Asp Asn Glu Asp Pro Gln Val Asn Ile Val Glu Glu Asp Pro Leu
                405                 410                 415

Asn Ser Gly Asp Asp Val Ser Glu Gln Asp Val Pro Asp Leu Phe Asp
            420                 425                 430

Thr Asp Asn Val Ile Val Cys Gln Tyr Asp Lys Ile His Arg Ser Lys
        435                 440                 445
```

```
Asn Lys Trp Lys Phe Tyr Leu Lys Asp Gly Val Met Cys Phe Gly Gly
    450                 455                 460

Arg Asp Tyr Val Phe Ala Lys Ala Ile Gly Asp Ala Glu Trp
465                 470                 475

<210> SEQ ID NO 3
<211> LENGTH: 3824
<212> TYPE: DNA
<213> ORGANISM: Homo sapien

<400> SEQUENCE: 3
ggactttggg actggacaga cctggtcaca gtctaggttc tacatcttac tggtcgagca      60
actttagagt caacctattt gatttcttga caagaccaca atctgatccc aaagatgtgc     120
tccacaaatc caggcaaatg ggtcaccttt gatgatgatc ctgctgttca atcttctcaa     180
aagtcaaaga attttcctct ggagaatcaa ggtgtctgta gaccaaatgg actgaagctg     240
aaccctcctg gcctcaggga atttcccagt ggatcttcct ccaccagcag cactcctctc     300
tcctccccca ttgtagattt ttatttcagt ccaggacctc aagtaactc tcctctttct      360 acacctacca aagacttccc aggttttcct ggcatcccca agcagggac tcatgtgctt      420 tatcctattc agaatcatc ttcagacagc ccactcgcaa tatcaggagg agaatcttcc      480
ttactgccta ccagaccaac atgtttatcc catgccttgt tacccagtga ccactcatgt     540
acacatccaa ctcccaaagt aggtcttcca gatgaagtta atcctcaaca ggctgaaagc     600
ctaggattcc aaagtgatga tctcccccag tttcagtatt ttcgagagga ctgtgctttt     660
tcaagtccat ttcggaaaga tgaaggcagt gattcccatt tcacccttga cccaccagga     720
agcaaaaaga tgttctcatc aagaaacaag gagatgccta ttgaccaaaa agcctaaat      780 aagtgttcac tcaactatat ctgtgagaag cttgaacatc tccagtcagc tgagaaccaa     840
gactcactta gaagtttgtc tatgcactgt ctatgtgctg aagaaaatgc ctcttccttt     900
gtcccccaca cactcttcag gagtcagcca aaatccggat ggtctttcat gctgagaatt     960
cctgagaaga agaatatgat gtcttcccgg caatggggac caattttct gaaagttttg     1020 cctggaggaa ttttgcagat gtattatgaa cagggattag aaaaaccatt taagagata     1080 cagcttgatc catattgtag gctttctgaa cccaaggttg agaacttcag tgtagcagga    1140
aaaatccaca ctgtgaagat tgaacatgtg tcttacacag aaaaaaggaa ataccattct    1200
aagacagaag tagttcatga acctgacata gagcagatgc tgaagttggg gtccacatcg    1260
taccatgact tccttgactt tctgactact gtggaggagg agctgatgaa gttgccagct    1320
gtttcaaaac caaaaaagaa ctacgaggag caagaaattt ccttggaaat tgtggacaac    1380
ttttggggta aagtcacaaa agaaggaaaa tttgttgaaa gtgctgtgat aactcaaatt    1440
tattgcctct gctttgtgaa tgggaacctg gaatgctttt taaccttgaa tgaccttgag    1500
ttgccgaagc gagatgaatc ctattatgag aaggactcag aaaaaagggg gattgatatt    1560
cttgactacc attttcataa gtgtgtgaat gtacaagaat ttgagcaatc aagaatcatt    1620
aagtttgtac tctgctggat gctgccggtt gagctgatgc gtttcaagac tttgtataat    1680
ggggataatc ttcccttttc cttgaagtct gtagtggttg tccagggagc atacgtggaa    1740
cttcaggctt ttgtcaacat ggcctcattg gcgcagaggt catcctatgc tggttcctta    1800
aggtcctgtg acaatataag gatacacttt cctgtcccat cgcagtggat caaggccctt    1860
tggaccatga acctccagag gcagaagtct ctgaaagcta aaatgaaccg ccgagcatgt    1920
ctggggagtt tacaggaact tgaatctgaa cctgtcattc aagtcactgt ggggtcagca    1980
```

-continued

```
aaatatgaga gtgcctacca ggcagtggta tggaagatag atcggcttcc agacaaaaat    2040
tcaagtctag atcatcccca ttgtctgtca tacaaattag agcttggatc agaccaagaa    2100
attccctctg attggtatcc atttgctact gttcagtttt ccgtgcctga cacctgtgcc    2160
tcaaggacag aggtcaggtc tctgggagtg agagtgatg tccagccaca gaaacatgtt     2220
cagcagcgag cttgctacaa catccagcct aaactctaca gatctgtaat tgaagatgta    2280
attgaaggag ttcggaatct atttgctgaa aaggtatag aggaacaagt tttaaaagac     2340
ttgaagcagc tctgggaaac caaggttttg cagtctaaag caacagaaga cttcttcaga    2400
aatagcatcc aatcacctct gtttactctt cagttgccgc acagcttgca ccaaacattg    2460
caatcgtcaa cagcatcatt agttattcct gctggtagaa ctcttccaag ttttaccaca    2520
gcagaactgg gcacttcaaa ctccagtgca aactttactt ttcctggtta tcccattcat    2580
gtaccagcag gtgtgacact acagactgta tctggtcacc tttataaagt caatgtacca    2640
attatggtga cagagacttc tggaagagca ggtattcttc agcatccaat tcagcaagta    2700
tttcaacagc ttggccagcc ttcagtaata caaactagtg ttccacaatt gaatccatgg    2760
tctcttcaag caactactga aaaatcacag agaattgaaa ccgtgctaca gcaacccgca    2820
attctacctt ctgggccagt agataggaaa cacttagaaa atgccaccag tgatatactt    2880
gtatctcctg gaaatgagca taaaatcgtg cctgaagctt gttgtgtca tcaggaaagt     2940 tctcactata tcagtcttcc aggtgttgta ttttctccac aggtctctca acaaattct     3000 gatgtggagt cagtgctcag tggttcagct agcatggctc aaaatctgca tgatgagtcc    3060
ctctccacaa gccctcatgg ggctctccac cagcacgtga ctgatattca gcttcatatt    3120
cttaaaaata ggatgtatgg atgtgattct gtaaagcaac aagaaatat agaggaaccc      3180 agcaacatac ctgtatcaga aaggattct aattctcagg tggatttaag cattcgggtt     3240
actgatgatg atattggtga ataattcaa gtagatggaa gcggtgatac atcttccaat      3300
gaagaaatag gaagtacaag agatgcagat gagaatgaat ttctagggaa tattgacggg    3360
ggagatctga aggtacctga agaagaagct gacagtattt caaatgagga ttcagccaca    3420
aacagtagtg ataatgaaga ccctcaagta acattgtag aagaggaccc tttaaattct      3480
ggagatgatg ttagtgaaca ggatgtgcca gacctgtttg acacggataa tgtaattgtc    3540
tgtcagtatg ataagattca tcgaagcaag aacaaatgga aattctatt gaaagatggt      3600 gttatgtgtt ttggagggag agactatgta tttgcaaaag ccattggtga tgcagagtgg    3660
taaaccttgt gagctcagta catctatttt gtgaacatca gttggactat attgcatatt    3720
gtgaattcat ttttatttg aatatagtcc agcacagagc tgttcaaatt tttagttcac     3780
tgtatggaat ttaataaaat tataattcag atgcagatac aatt                     3824
```

<210> SEQ ID NO 4
<211> LENGTH: 1181
<212> TYPE: PRT
<213> ORGANISM: Homo sapien

<400> SEQUENCE: 4

```
Met Cys Ser Thr Asn Pro Gly Lys Trp Val Thr Phe Asp Asp Asp Pro
1               5                   10                  15

Ala Val Gln Ser Ser Gln Lys Ser Lys Asn Phe Pro Leu Glu Asn Gln
            20                  25                  30

Gly Val Cys Arg Pro Asn Gly Leu Lys Leu Asn Pro Pro Gly Leu Arg
        35                  40                  45
```

```
Glu Phe Pro Ser Gly Ser Ser Thr Ser Ser Thr Pro Leu Ser Ser
     50                  55                  60

Pro Ile Val Asp Phe Tyr Phe Ser Pro Gly Pro Ser Asn Ser Pro
 65                  70                  75                  80

Leu Ser Thr Pro Thr Lys Asp Phe Pro Gly Phe Pro Gly Ile Pro Lys
                 85                  90                  95

Ala Gly Thr His Val Leu Tyr Pro Ile Pro Glu Ser Ser Asp Ser
                100                 105                 110

Pro Leu Ala Ile Ser Gly Gly Glu Ser Ser Leu Leu Pro Thr Arg Pro
                115                 120                 125

Thr Cys Leu Ser His Ala Leu Leu Pro Ser Asp His Ser Cys Thr His
    130                 135                 140

Pro Thr Pro Lys Val Gly Leu Pro Asp Glu Val Asn Pro Gln Gln Ala
145                 150                 155                 160

Glu Ser Leu Gly Phe Gln Ser Asp Asp Leu Pro Gln Phe Gln Tyr Phe
                165                 170                 175

Arg Glu Asp Cys Ala Phe Ser Ser Pro Phe Arg Lys Asp Glu Gly Ser
                180                 185                 190

Asp Ser His Phe Thr Leu Asp Pro Pro Gly Ser Lys Lys Met Phe Ser
                195                 200                 205

Ser Arg Asn Lys Glu Met Pro Ile Asp Gln Lys Ser Leu Asn Lys Cys
    210                 215                 220

Ser Leu Asn Tyr Ile Cys Glu Lys Leu Glu His Leu Gln Ser Ala Glu
225                 230                 235                 240

Asn Gln Asp Ser Leu Arg Ser Leu Ser Met His Cys Leu Cys Ala Glu
                245                 250                 255

Glu Asn Ala Ser Ser Phe Val Pro His Thr Leu Phe Arg Ser Gln Pro
                260                 265                 270

Lys Ser Gly Trp Ser Phe Met Leu Arg Ile Pro Glu Lys Lys Asn Met
    275                 280                 285

Met Ser Ser Arg Gln Trp Gly Pro Ile Phe Leu Lys Val Leu Pro Gly
    290                 295                 300

Gly Ile Leu Gln Met Tyr Tyr Glu Gln Gly Leu Glu Lys Pro Phe Lys
305                 310                 315                 320

Glu Ile Gln Leu Asp Pro Tyr Cys Arg Leu Ser Glu Pro Lys Val Glu
                325                 330                 335

Asn Phe Ser Val Ala Gly Lys Ile His Thr Val Lys Ile Glu His Val
                340                 345                 350

Ser Tyr Thr Glu Lys Arg Lys His Ser Lys Thr Glu Val Val His Glu
                355                 360                 365

Pro Asp Ile Glu Gln Met Leu Lys Leu Gly Ser Thr Ser Tyr His Asp
    370                 375                 380

Phe Leu Asp Phe Leu Thr Thr Val Glu Glu Leu Met Lys Leu Pro
385                 390                 395                 400

Ala Val Ser Lys Pro Lys Lys Asn Tyr Glu Glu Gln Glu Ile Ser Leu
                405                 410                 415

Glu Ile Val Asp Asn Phe Trp Gly Lys Val Thr Lys Glu Gly Lys Phe
                420                 425                 430

Val Glu Ser Ala Val Ile Thr Gln Ile Tyr Cys Leu Cys Phe Val Asn
                435                 440                 445

Gly Asn Leu Glu Cys Phe Leu Thr Leu Asn Asp Leu Glu Leu Pro Lys
    450                 455                 460
```

```
Arg Asp Glu Ser Tyr Tyr Glu Lys Asp Ser Glu Lys Lys Gly Ile Asp
465                 470                 475                 480

Ile Leu Asp Tyr His Phe His Lys Cys Val Asn Val Gln Glu Phe Glu
            485                 490                 495

Gln Ser Arg Ile Ile Lys Phe Val Pro Leu Asp Ala Cys Arg Phe Glu
            500                 505                 510

Leu Met Arg Phe Lys Thr Leu Tyr Asn Gly Asp Asn Leu Pro Phe Ser
            515                 520                 525

Leu Lys Ser Val Val Val Gln Gly Ala Tyr Val Glu Leu Gln Ala
    530                 535                 540

Phe Val Asn Met Ala Ser Leu Ala Gln Arg Ser Ser Tyr Ala Gly Ser
545                 550                 555                 560

Leu Arg Ser Cys Asp Asn Ile Arg Ile His Phe Pro Val Pro Ser Gln
            565                 570                 575

Trp Ile Lys Ala Leu Trp Thr Met Asn Leu Gln Arg Gln Lys Ser Leu
            580                 585                 590

Lys Ala Lys Met Asn Arg Arg Ala Cys Leu Gly Ser Leu Gln Glu Leu
            595                 600                 605

Glu Ser Glu Pro Val Ile Gln Val Thr Val Gly Ser Ala Lys Tyr Glu
610                 615                 620

Ser Ala Tyr Gln Ala Val Val Trp Lys Ile Asp Arg Leu Pro Asp Lys
625                 630                 635                 640

Asn Ser Ser Leu Asp His Pro His Cys Leu Ser Tyr Lys Leu Glu Leu
            645                 650                 655

Gly Ser Asp Gln Glu Ile Pro Ser Asp Trp Tyr Pro Phe Ala Thr Val
            660                 665                 670

Gln Phe Ser Val Pro Asp Thr Cys Ala Ser Arg Thr Glu Val Arg Ser
            675                 680                 685

Leu Gly Val Glu Ser Asp Val Gln Pro Gln Lys His Val Gln Gln Arg
    690                 695                 700

Ala Cys Tyr Asn Ile Gln Pro Lys Leu Tyr Arg Ser Val Ile Glu Asp
705                 710                 715                 720

Asp Val Ile Glu Gly Val Arg Asn Leu Phe Ala Glu Glu Gly Ile Glu
            725                 730                 735

Gln Val Leu Lys Asp Leu Lys Gln Leu Trp Glu Thr Lys Val Leu Gln
            740                 745                 750

Ser Lys Ala Thr Glu Asp Phe Phe Arg Asn Ser Ile Gln Ser Pro Leu
    755                 760                 765

Phe Thr Leu Gln Leu Pro His Ser Leu His Gln Thr Leu Gln Ser Ser
770                 775                 780

Thr Ala Ser Leu Val Ile Pro Ala Gly Arg Thr Leu Pro Ser Phe Thr
785                 790                 795                 800

Thr Ala Glu Leu Gly Thr Ser Asn Ser Ser Ala Asn Phe Thr Phe Pro
            805                 810                 815

Gly Tyr Pro Ile His Val Pro Ala Gly Val Thr Leu Gln Thr Val Ser
            820                 825                 830

Gly His Leu Tyr Lys Val Asn Val Pro Ile Met Val Thr Glu Thr Ser
            835                 840                 845

Gly Arg Ala Gly Ile Leu Gln His Pro Ile Gln Gln Val Phe Gln Gln
    850                 855                 860

Leu Gly Gln Pro Ser Val Ile Gln Thr Ser Val Pro Gln Leu Asn Pro
865                 870                 875                 880

Trp Ser Leu Gln Ala Thr Thr Glu Lys Ser Gln Arg Ile Glu Thr Val
```

```
                            885                890                895
Leu Gln Gln Pro Ala Ile Leu Pro Ser Gly Pro Val Asp Arg Lys His
            900                905                910

Leu Glu Asn Ala Thr Ser Asp Ile Leu Val Ser Pro Gly Asn Glu His
        915                920                925

Lys Ile Val Pro Glu Ala Leu Leu Cys His Gln Glu Ser Ser His Tyr
    930                935                940

Ile Ser Leu Pro Gly Val Val Phe Ser Pro Gln Val Ser Gln Thr Asn
945                950                955                960

Ser Asp Val Glu Ser Val Leu Ser Gly Ser Ala Ser Met Ala Gln Asn
            965                970                975

Leu His Asp Glu Ser Leu Ser Thr Ser Pro His Gly Ala Leu His Gln
        980                985                990

His Val Thr Asp Ile Gln Leu His  Ile Leu Lys Asn Arg  Met Tyr Gly
        995                1000                1005

Cys Asp  Ser Val Lys Gln Pro  Arg Asn Ile Glu Glu  Pro Ser Asn
    1010                1015                1020

Ile Pro  Val Ser Glu Lys Asp  Ser Asn Ser Gln Val  Asp Leu Ser
    1025                1030                1035

Ile Arg  Val Thr Asp Asp  Ile Gly Glu Ile  Gln Val Asp
    1040                1045                1050

Gly Ser  Gly Asp Thr Ser Ser  Asn Glu Glu Ile Gly  Ser Thr Arg
    1055                1060                1065

Asp Ala  Asp Glu Asn Glu Phe  Leu Gly Asn Ile Asp  Gly Gly Asp
    1070                1075                1080

Leu Lys  Val Pro Glu Glu Glu  Ala Asp Ser Ile Ser  Asn Glu Asp
    1085                1090                1095

Ser Ala  Thr Asn Ser Ser Asp  Asn Glu Asp Pro Gln  Val Asn Ile
    1100                1105                1110

Val Glu  Glu Asp Pro Leu Asn  Ser Gly Asp Asp Val  Ser Glu Gln
    1115                1120                1125

Asp Val  Pro Asp Leu Phe Asp  Thr Asp Asn Val Ile  Val Cys Gln
    1130                1135                1140

Tyr Asp  Lys Ile His Arg Ser  Lys Asn Lys Trp Lys  Phe Tyr Leu
    1145                1150                1155

Lys Asp  Gly Val Met Cys Phe  Gly Gly Arg Asp Tyr  Val Phe Ala
    1160                1165                1170

Lys Ala  Ile Gly Asp Ala Glu  Trp
    1175                1180

<210> SEQ ID NO 5
<211> LENGTH: 253
<212> TYPE: DNA
<213> ORGANISM: Homo sapien
<220> FEATURE:
<221> NAME/KEY: CDS
<222> LOCATION: (1)..(30)
<223> OTHER INFORMATION:

<400> SEQUENCE: 5 gca ttc cca aga agg aca tcg ttt aac acc taaactcatt taacaaagga        50
Ala Phe Pro Arg Arg Thr Ser Phe Asn Thr
1               5                   10 tccgagaaga acagggacag tgtgggaaga aatcttcttg tgatggcata tttgcttcct   110
atatttcttc tggaatcatg ttcgcttggc ttcctgatta aaaacacagt tttattgctc   170
```

-continued tctgcactgc caaaccaata aatttacaga agagaaagct gtattccact gtaccccttg    230
cagcatcaat aaaactgaca gcc                                            253

<210> SEQ ID NO 6
<211> LENGTH: 10
<212> TYPE: PRT
<213> ORGANISM: Homo sapien

<400> SEQUENCE: 6

Ala Phe Pro Arg Arg Thr Ser Phe Asn Thr
1               5                   10

<210> SEQ ID NO 7
<211> LENGTH: 10
<212> TYPE: PRT
<213> ORGANISM: Homo sapien

<400> SEQUENCE: 7

Ala Phe Pro Arg Arg Thr Ser Phe Asn Thr
1               5                   10

<210> SEQ ID NO 8
<211> LENGTH: 18
<212> TYPE: DNA
<213> ORGANISM: Homo sapien

<400> SEQUENCE: 8
agaaattccc tctgattg                                                   18

<210> SEQ ID NO 9
<211> LENGTH: 18
<212> TYPE: DNA
<213> ORGANISM: Homo sapien

<400> SEQUENCE: 9
agtaacccga atgcttaa                                                   18

<210> SEQ ID NO 10
<211> LENGTH: 18
<212> TYPE: DNA
<213> ORGANISM: Homo sapien

<400> SEQUENCE: 10
atgctagctg aaccactg                                                   18

<210> SEQ ID NO 11
<211> LENGTH: 29
<212> TYPE: DNA
<213> ORGANISM: Homo sapien

<400> SEQUENCE: 11
ggagtttgaa gtgcccaggt ctgctgtgg                                       29

<210> SEQ ID NO 12
<211> LENGTH: 30
<212> TYPE: DNA
<213> ORGANISM: Homo sapien

<400> SEQUENCE: 12
ccagaaggta gaattgcggg ttgctgtagc                                      30

<210> SEQ ID NO 13
<211> LENGTH: 28

```
<212> TYPE: DNA
<213> ORGANISM: Homo sapien

<400> SEQUENCE: 13
ggtgctgtca tggcctgcct caacccgg                                           28

<210> SEQ ID NO 14
<211> LENGTH: 54
<212> TYPE: DNA
<213> ORGANISM: Homo sapien

<400> SEQUENCE: 14
actactcata tggcacacca tcaccatcac catgtaccta aactctacag atct             54

<210> SEQ ID NO 15
<211> LENGTH: 30
<212> TYPE: DNA
<213> ORGANISM: Homo sapien

<400> SEQUENCE: 15
agtagtggat ccttaccact ctgcatcacc                                         30

<210> SEQ ID NO 16
<211> LENGTH: 24
<212> TYPE: PRT
<213> ORGANISM: Homo sapien

<400> SEQUENCE: 16

Met Glu Thr His Ile Ser His Ile Ser His Ile Ser His Ile Ser His
1               5                   10                  15

Ile Ser His Ile Ser Val Ala Leu
            20

<210> SEQ ID NO 17
<211> LENGTH: 6
<212> TYPE: PRT
<213> ORGANISM: Homo sapien

<400> SEQUENCE: 17

Met Ala Cys Leu Asn Pro
1               5

<210> SEQ ID NO 18
<211> LENGTH: 23
<212> TYPE: DNA
<213> ORGANISM: Homo sapien

<400> SEQUENCE: 18
tactgctcga gcaactttag agt                                                23
```